(12) United States Patent
Kozlowski et al.

(10) Patent No.: US 10,098,865 B2
(45) Date of Patent: Oct. 16, 2018

(54) MULTI-ARM POLYMERIC PRODRUG CONJUGATES OF TAXANE-BASED COMPOUNDS

(71) Applicant: Nektar Therapeutics, San Francisco, CA (US)

(72) Inventors: Antoni Kozlowski, Huntsville, AL (US); Timothy A. Riley, Worcester, MA (US); Samuel P. McManus, Guntersville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 15/045,077

(22) Filed: Feb. 16, 2016

(65) Prior Publication Data

US 2016/0235705 A1     Aug. 18, 2016

Related U.S. Application Data

(63) Continuation of application No. 13/995,287, filed as application No. PCT/US2011/066853 on Dec. 22, 2011, now abandoned.

(60) Provisional application No. 61/426,227, filed on Dec. 22, 2010.

(51) Int. Cl.
```
A61K 31/337    (2006.01)
A61K 47/60     (2017.01)
C07D 305/14    (2006.01)
C08G 65/329    (2006.01)
C08G 65/333    (2006.01)
```

(52) U.S. Cl.
CPC .......... *A61K 31/337* (2013.01); *A61K 47/60* (2017.08); *C07D 305/14* (2013.01); *C08G 65/329* (2013.01); *C08G 65/33337* (2013.01); *C08L 2203/02* (2013.01)

(58) Field of Classification Search
CPC .......... A61K 31/337; A61K 47/48215; C08G 65/33337; C08G 65/329; C07D 305/14; C08L 2203/02
See application file for complete search history.

(56) References Cited

U.S. PATENT DOCUMENTS

| | | |
|---|---|---|
| 4,665,077 A | 5/1987 | Stringfellow et al. |
| 4,670,417 A | 6/1987 | Iwasaki et al. |
| 4,810,646 A | 3/1989 | Jamas et al. |
| 4,814,470 A | 3/1989 | Colin et al. |
| 4,992,540 A | 2/1991 | Jamas et al. |
| 5,028,703 A | 7/1991 | Jamas et al. |
| 5,149,820 A | 9/1992 | Borretzen et al. |
| 5,159,081 A | 10/1992 | Cantrell et al. |
| 5,250,542 A | 10/1993 | Cantrell et al. |
| 5,252,714 A | 10/1993 | Harris et al. |
| 5,270,328 A | 12/1993 | Cantrell et al. |
| 5,281,698 A | 1/1994 | Nitecki |
| 5,294,637 A | 3/1994 | Chen et al. |
| 5,321,095 A | 6/1994 | Greenwald |
| 5,434,171 A | 7/1995 | Frank et al. |
| 5,438,072 A | 8/1995 | Bobee et al. |
| 5,468,478 A | 11/1995 | Saifer et al. |
| 5,476,954 A | 12/1995 | Bourzat et al. |
| 5,607,677 A | 3/1997 | Jamas et al. |
| 5,614,549 A | 3/1997 | Greenwald et al. |
| 5,629,384 A | 5/1997 | Veronese et al. |
| 5,648,506 A | 7/1997 | Desai et al. |
| 5,650,234 A | 7/1997 | Dolence et al. |
| 5,672,662 A | 9/1997 | Harris et al. |
| 5,681,567 A | 10/1997 | Martinez et al. |
| 5,688,977 A | 11/1997 | Sisti et al. |
| 5,698,582 A | 12/1997 | Bastart et al. |
| 5,733,984 A | 3/1998 | Nakahara et al. |
| 5,739,208 A | 4/1998 | Harris |
| 5,741,495 A | 4/1998 | Jamas et al. |
| 5,756,776 A | 5/1998 | Bombardelli et al. |
| 5,824,784 A | 10/1998 | Kinstler et al. |
| 5,840,900 A | 11/1998 | Greenwald et al. |
| 5,846,514 A | 12/1998 | Foster et al. |
| 5,847,170 A | 12/1998 | Bouchard et al. |
| 5,859,022 A | 1/1999 | Hausheer et al. |
| 5,871,732 A | 2/1999 | Burkly et al. |
| 5,880,131 A | 3/1999 | Greenwald et al. |
| 5,895,660 A | 4/1999 | Hoffmann et al. |
| 5,900,461 A | 5/1999 | Harris |

(Continued)

FOREIGN PATENT DOCUMENTS

| | | |
|---|---|---|
| AU | 9481470 B | 2/1998 |
| CN | 101422613 | 5/2009 |

(Continued)

OTHER PUBLICATIONS

Iwao Ojima and John C. Slater, Synthesis of Novel 3-Trifluoromethyl Taxoids Through Effective Kinetic Resolution of Racemic 4-CF3-b-Lactams With Baccatins, CHIRALITY 9:487-494 (1997).*
WO 95/13271; machine translation.*
Abuchowski et al., "Cancer Therapy with Chemically Modified Enzymes. I. Antitumor Properties of Polyethylene Glycol-Asparaginase Conjugates," Cancer Biochem. Biophys., vol. 7, pp. 175-186, (1984).
Andresz et al., "Chemische Synthese verzweigter Polysaccharide, 5," Makromol. Chem., vol. 179, pp. 301-312, (1978).
Bacchi et al., "Novel Synthetic Polyamines Are Effective in the Treatment of Experimental Microsporidiosis, an Opportunistic AIDS-Associated Infection," Antimicrobial Agents and Chemotherapy, vol. 46, No. 1, pp. 55-61, (Jan. 2002).

(Continued)

*Primary Examiner* — Sarah Pihonak
*Assistant Examiner* — Jason Deck
(74) *Attorney, Agent, or Firm* — Susan T. Evans

(57) ABSTRACT

Among other aspects, provided herein are multi-arm polymeric prodrug conjugates of taxane-based compounds and/or fluorinated forms thereof. Methods of preparing such conjugates as well as methods of administering the conjugates are also provided. Upon administration to a patient, release of the taxane-based compound is achieved.

3 Claims, 1 Drawing Sheet

(56) References Cited

U.S. PATENT DOCUMENTS

| | | |
|---|---|---|
| 5,914,311 A | 6/1999 | Barenholz et al. |
| 5,922,675 A | 7/1999 | Baker et al. |
| 5,932,462 A | 8/1999 | Harris et al. |
| 5,962,705 A | 10/1999 | Didier et al. |
| 5,965,566 A | 10/1999 | Greenwald et al. |
| 6,011,042 A | 1/2000 | Greenwald et al. |
| 6,018,073 A | 1/2000 | Holton et al. |
| 6,121,451 A | 9/2000 | Henegar et al. |
| 6,124,482 A | 9/2000 | Ramadoss et al. |
| 6,127,355 A | 10/2000 | Greenwald et al. |
| 6,136,310 A | 10/2000 | Hanna et al. |
| 6,153,655 A | 11/2000 | Martinez et al. |
| 6,194,580 B1 | 2/2001 | Greenwald et al. |
| 6,331,635 B1 | 12/2001 | Bouchard et al. |
| 6,346,543 B1 | 2/2002 | Bissery et al. |
| 6,362,254 B2 | 3/2002 | Harris et al. |
| 6,372,780 B2 | 4/2002 | Bouchard et al. |
| 6,387,946 B1 | 5/2002 | Bouchard et al. |
| 6,395,266 B1 | 5/2002 | Martinez et al. |
| 6,403,569 B1 | 6/2002 | Achterrath |
| 6,403,634 B1 | 6/2002 | Bissery |
| 6,461,603 B2 | 10/2002 | Bentley et al. |
| 6,495,659 B2 | 12/2002 | Bentley et al. |
| 6,602,977 B1 | 8/2003 | Ljungqvist et al. |
| 6,608,076 B1 | 8/2003 | Greenwald et al. |
| 6,649,778 B1 | 11/2003 | Zhao et al. |
| 6,740,734 B1 | 5/2004 | Nilsson et al. |
| 6,955,877 B1 | 10/2005 | Nygren et al. |
| 7,026,440 B2 | 4/2006 | Bentley et al. |
| 7,186,851 B2 | 3/2007 | Baloglu |
| 7,241,907 B2 | 7/2007 | Didier et al. |
| 7,267,941 B2 | 9/2007 | Snell et al. |
| 7,744,861 B2 | 6/2010 | Zhao et al. |
| 8,637,466 B2 | 1/2014 | Kozlowski et al. |
| 8,962,556 B2 | 2/2015 | Kozlowski et al. |
| 8,962,566 B2 | 2/2015 | Kozlowski et al. |
| 9,199,954 B2 | 12/2015 | Kozlowski et al. |
| 9,220,790 B2 | 12/2015 | Kozlowski et al. |
| 9,504,755 B2 | 11/2016 | Kozlowski et al. |
| 2001/0041172 A1 | 11/2001 | Bentley et al. |
| 2002/0182172 A1 | 12/2002 | Bentley et al. |
| 2003/0105275 A1 | 6/2003 | Bentley et al. |
| 2004/0037802 A1 | 2/2004 | Zhao et al. |
| 2004/0058981 A1 | 3/2004 | Lai et al. |
| 2004/0077595 A1 | 4/2004 | Cheng et al. |
| 2005/0009988 A1 | 1/2005 | Harris et al. |
| 2005/0036978 A1 | 2/2005 | Kozlowski |
| 2005/0112088 A1 | 5/2005 | Zhao et al. |
| 2005/0281781 A1 | 12/2005 | Ostroff |
| 2006/0051346 A1 | 3/2006 | Wijdenes |
| 2006/0105046 A1 | 5/2006 | Bentley et al. |
| 2006/0182716 A1 | 8/2006 | Hong et al. |
| 2006/0204473 A1 | 9/2006 | Blatt et al. |
| 2007/0009988 A1 | 1/2007 | Monod et al. |
| 2007/0025956 A1 | 2/2007 | Burton et al. |
| 2007/0197575 A1 | 8/2007 | Zhao et al. |
| 2008/0044438 A1 | 2/2008 | Ostroff et al. |
| 2008/0207913 A1 | 8/2008 | Breitenkamp et al. |
| 2008/0262250 A1 | 10/2008 | Naidu |
| 2009/0016957 A1 | 1/2009 | Nilsson et al. |
| 2009/0069410 A1 | 3/2009 | Czarnik |
| 2009/0074848 A1 | 3/2009 | Alesix et al. |
| 2009/0143363 A1 | 6/2009 | Liu |
| 2009/0239886 A1 | 9/2009 | Tung et al. |
| 2010/0048868 A1 | 2/2010 | Carlsson et al. |
| 2010/0247669 A1 | 9/2010 | Eliasof et al. |
| 2011/0020223 A1 | 1/2011 | Abrahmsen et al. |
| 2011/0200550 A1 | 8/2011 | Kozlowksi et al. |
| 2013/0331443 A1 | 12/2013 | Kozlowski et al. |
| 2013/0338216 A1 | 12/2013 | Kozlowski et al. |
| 2013/0345298 A1 | 12/2013 | Kozlowski |
| 2014/0088021 A1 | 3/2014 | Riggs-Sauthier et al. |
| 2014/0113961 A1 | 4/2014 | Kozlowski et al. |
| 2015/0133534 A1 | 5/2015 | Kozlowski et al. |
| 2016/0235705 A1 | 8/2016 | Kozlowski et al. |

FOREIGN PATENT DOCUMENTS

| | | | |
|---|---|---|---|
| EP | 0 336 841 | 5/1993 | |
| EP | 0 512 112 | 5/1997 | |
| EP | 0 757 049 | 3/1999 | |
| EP | 0 840 618 | 4/2003 | |
| EP | 0 617 018 | 10/2003 | |
| EP | 0 923 566 | 10/2003 | |
| EP | 1 266 965 | 5/2006 | |
| EP | 0 854 885 | 12/2006 | |
| EP | 2 108 368 | 10/2009 | |
| WO | WO 90/10443 | 9/1990 | |
| WO | WO 94/07878 | 4/1994 | |
| WO | WO 9513271 A1 * | 5/1995 | ........... C07D 305/14 |
| WO | WO 95/26967 | 10/1995 | |
| WO | WO 96/30335 | 10/1996 | |
| WO | WO 96/40749 | 12/1996 | |
| WO | WO 97/33552 | 9/1997 | |
| WO | WO 97/46697 | 12/1997 | |
| WO | WO 98/41562 | 9/1998 | |
| WO | WO 99/53951 | 10/1999 | |
| WO | WO 00/63243 | 10/2000 | |
| WO | WO 00/64486 | 11/2000 | |
| WO | WO 01/43779 | 6/2001 | |
| WO | WO 01/46291 | 6/2001 | |
| WO | WO 01/62299 | 8/2001 | |
| WO | WO 01/62827 | 8/2001 | |
| WO | WO 01/74402 | 10/2001 | |
| WO | WO 02/08789 | 1/2002 | |
| WO | WO 02/43772 | 6/2002 | |
| WO | WO 03/031467 | 4/2003 | |
| WO | WO 03/037384 | 5/2003 | |
| WO | WO 03/037385 | 5/2003 | |
| WO | WO 2004/012773 | 2/2004 | |
| WO | WO 2004/060967 | 7/2004 | |
| WO | WO 2005/028539 | 3/2005 | |
| WO | WO 2005/107815 | 11/2005 | |
| WO | WO 2005/108463 | 11/2005 | |
| WO | WO 2007/065869 | 6/2007 | |
| WO | WO 2007/098466 | 8/2007 | |
| WO | WO 2008/052322 | 5/2008 | |
| WO | WO 2008/066902 | 6/2008 | |
| WO | WO 2008/106186 | 9/2008 | |
| WO | WO 2009/080810 | 7/2009 | |
| WO | WO 2010/019233 | 2/2010 | |
| WO | WO 2012/088391 | 6/2012 | |
| WO | WO 2012/088433 | 6/2012 | |
| WO | WO 2012/088445 | 6/2012 | |
| WO | WO 2012/166555 | 12/2012 | |

OTHER PUBLICATIONS

Beauchamp et al., "A New Procedure for the Synthesis of Polyethylene Glycol-Protein Adducts; Effects on Function, Receptor Recognition, and Clearance of Superoxide Dismutase, Lactoferrin, and $\alpha_2$-Macroglobulin," Analytical Biochemistry, vol. 131, pp. 25-33, (1983).

Brinkley, "A Brief Survey of Methods for Preparing Protein Conjugates with Dyes, Haptens, and Cross-Linking Reagents", Bioconjugate Chem., vol. 3, pp. 2-13, (1992).

Buckmann et al., "Functionalization of Poly(ethylene glycol) and Monomethoxy-Poly(ethylene glycol)," Makromol. Chem., vol. 182, pp. 1379-1384, (1981).

Elling et al., "Immunoaffinity Partitioning: Synthesis and Use of Polyethylene Glycol-Oxirane for Coupling to Bovine Serum Albumin and Monoclonal Antibodies," Biotechnology and Applied Biochemistry, vol. 13, pp. 354-362, (1991).

Foster, "Deuterium Isotope Effects in the Metabolism of Drugs and Xenobiotics: Implications for Drug Design," Advances in Drug Research, vol. 14, pp. 1-40, (1985).

Goodson et al., "Site-Directed Pegylation of Recombinant Interleukin-2 at its Glycosylation Site," Biotechnology, vol. 8, pp. 343-346, (Apr. 1990).

Harris et al., "Synthesis and Characterization of Poly(ethylene Glycol) Derivatives," Journal of Polymer Science: Polymer Chemistry Edition, vol. 22, pp. 341-352, (1984).

(56) References Cited

OTHER PUBLICATIONS

Joppich et al., "Peptides Flanked by Two Polymer Chains, 1: Synthesis of Glycyl-L-tryptophylglycine Substituted by Poly(ethylene oxide) at both the Carboxy and the Amino End Groups," Makromol. Chem., vol. 180, pp. 1381-1384, (1979).
Kogan, "The Synthesis of Substituted Methoxy-Poly(Ethylene Glycol) Derivatives Suitable for Selective Protein Modification," Synthetic Communications, vol. 22, No. 16, pp. 2417-2424, (1992).
Lu et al., "Design, synthesis and biological evaluation of novel fluorinated docetaxel analogues," European Journal of Medicinal Chemistry, vol. 44, pp. 482-491, (2009).
Olson et al., "Preparation and Characterization of Poly(ethylene glycol)ylated Human Growth Hormone Antagonist," American Chemical Society, Chapter 12, pp. 170-181, (1997).
Pitha et al., "Detergents Linked to Polysaccharides: Preparation and Effects on Membranes and Cells," Eur. J. Biochem., vol. 94, pp. 11-18, (1979).
Romani et al., "Synthesis of Unsymmetrical Cystine Peptides: Directed Disulfide Pairing with the Sulfenohydrazide Method," Chemistry of Peptides and Proteins, vol. 2, pp. 29-34, (1984).
Sartore et al., "Enzyme Modification by MPEG with an Amino Acid or Peptide as Spacer Arms," Applied Biochemistry and Biotechnology, vol. 27, pp. 45-54, (1991).
Sawhney et al., "Bioerodible Hydrogels Based on Photopolymerized Poly(ethylene glycol)-co-poly($\alpha$-hydroxy acid) Diacrylate Macromers," Macromolecules, vol. 26, pp. 581-587, (1993).
Tellingen et al., "Rapid Esterase-sensitive Breakdown of Polysorbate 80 and Its Impact on the Plasma Pharmacokinetics of Docetaxel and Metabolites in Mice," Clinical Cancer Research, vol. 5, pp. 2918-2924, (Oct. 1999).
Tondelli et al., "Poly(Ethylene Glycol) Imidazolyl Formates as Oligomeric Drug-Binding Matrices," Journal of Controlled Release, vol. 1, pp. 251-257, (1985).
Veronese et al., "Surface Modification of Proteins: Activation of Monomethoxy-Polyethylene Glycols by Phenylchloroformates and Modification of Ribonuclease and Superoxide Dismutase," Applied Biochemistry and Biotechnology, vol. 11, pp. 141-152, (1985).
Woghiren et al., "Protected Thiol-Polyethylene Glycol: A New Activated Polymer for Reversible Protein Modification," Bioconjugate Chem., vol. 4, pp. 314-318, (1993).
Zalipsky et al., "Attachment of Drugs to Polyethylene Glycols," Eur. Polym. J., vol. 19, No. 12, pp. 1177-1183, (1983).
PCT International Search Report and Written Opinion corresponding to PCT Application No. PCT/US2011/066853 dated Mar. 5, 2012.
PCT International Preliminary Report on Patentability corresponding to PCT Application No. PCT/US2011/066853 dated Jul. 4, 2013.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Ahlgren et al., "Targeting of HER2-Expressing Tumors with a Site-Specifically $^{99m}$Tc-Labeled Recombinant Affibody Molecule, $Z_{HER2:2395}$; with C-Terminally Engineered Cysteine," J. Nucl. Med. vol. 50, pp. 781-789, (2009).
Alexis et al., "GER-2-Targeted Nanoparticle-Affibody Bioconjugates for Cancer Therapy," Chem. Med. Chem., vol. 3, pp. 1839-1843, (2008).
Astruc et al., "Dendritic Catalysts and Dendrimers in Catalysis," Chem. Rev., vol. 101, pp. 2991-3023, (2001).
Baranay et al., "A New Amino Protecting Group Removable by Reduction, Chemistry of the Dithiasuccinoyl (Dts) Function," J. Am. Chem. Soc, vol. 116, pp. 7363-7365, (1977).
Benoiton et al., "2-Alkoxy-5(4H)-oxazolones from N-alkoxycarbonylamino acids and their implications in carbodiimide-mediated reactions in peptide synthesis'," Can. J. Chem., vol. 59, pp. 384-389, (1981).
Beuttler et al., "Targeting of Epidermal Growth Factor Receptor (EGFR)-Expressing Tumor Cells with Sterically Stabilized Affibody Liposomes (SAL)," Bioconjugate Chem., vol. 20, pp. 1201-1208, (2009).
Bono et al., "Cabazitaxel or mitoxantrone with prednisone in patients with metastatic castration-resistant prostate cancer (mCRPC) previously treated with docetaxel: Final results of a multinational phase III trial (TROPIC)," J. of Clin. Oncol. vol. 28, No. 15, 4508, abstract, (May 2010).
Bouchet et al., "Cabazitaxel, A New Taxane with Favorable Properties," Drugs of Today, vol. 46, No. 10, pp. 735-742, (2010).
Bouhlal et al., "Natural Antibodies to CCR5 from Breast Milk Block Infection of Macrophages and Dendritic Cells with Primary R5-Tropic HIV-1[1]," J. Immunol. vol. 174, pp. 7202-7209 (2005).
Burris et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," J. Clin. Oncology, vol. 29, No. 4, pp. 398-405 (2011).
Carnec et al. "Anti-CSCR4 Monoclonal Antibodies Recognizing Overlapping Epitopes Differ Significantly in Their Ability to Inhibit Entry of Human Immunodeficiency Virus Type 1," J. Virology, vol. 79, pp. 1930-1933, (2005).
Conover et al., "Camptothecin delivery systems: enhanced efficacy and tumor accumulation of camptothecin following its conjugation to polyethylene glycol via a glycine linker," Can. Chemother. Pharmacol., vol. 42, pp. 407-414, (1998).
Conover et al., "Camptothecin delivery systems: the utility of amino acid spacers for the conjugation of camptothecin with polyethylene glycol to create prodrugs," Anti-Cancer Drug Des., vol. 14, pp. 499-506, (1999).

(56) References Cited

OTHER PUBLICATIONS

Cook et al., "Species Dependent Esterase Activities for Hydrolysis of an Anti-HIV Prodrug Glycovir and Bioavailability of Active SC-48334," Pharmaceut. Res., vol. 12, No. 8, pp. 1158-1164, (1995).
De Bruijn et al., "Quantification of cabazitaxel in human plasma by liquid chromatography/triple-quadrupole mass spectrometry: A practical solution for non-specific binding," Journal of Pharmaceutical and Biomedical Analysis, vol. 59, pp. 117-122, (2012).
Degreef et al., "Antifungal azoles for skin disorders," Expert Opinion Ther. Patents, vol. 16, No. 9, pp. 1235-1253, (2006).
De Jesus et al., "Polyester Dendritic Systems for Drug Delivery Applications: In Vitro and In Vivo Evaluation," Bioconj. Chem., vol. 13, pp. 453-461, (2002).
Deutsch et al, "Synthesis of Congeners and Prodrugs. 3. Water-Soluble Prodrugs of Taxol with Potent Antitumor Activity," J. Med. Chem., vol. 32, No. 4, pp. 788-792, (1989).
Dubois, "Recent progress in the development of docetaxel and paclitaxel analogues," Expert Opin. Ther. Patents, vol. 16, No. 11, pp. 1481-1496, (2006).
Dumont, "Perspectives dans l'utilisation de molecules deuteriees en tant qu' agents therapeutiques," Revue IRE, vol. 6, No. 4, pp. 2-10, (1982).
Dutta et al., "A One-step Synthesis of a Deuterated Paclitaxel Analogue: 10-Deacetoxy-(10α-$^2$H) Paclitaxel," Bioorganic & Medicinal Chemistry Letters, vol. 9, pp. 3277-3278, (1999).
Ericsson et al., "In vitro hydrolysis rate and protein binding of clevidipine, a new ultrashort-acting calcium antagonist metabolised by esterases, in different animal species and man," Euro. J. of Pharmaceut. Sci., vol. 8, pp. 29-37, (1999).
Fang et al., "Synthesis and Antitumor Activity of C-2/C-10 Modified Analogues of Docetaxel," Chinese Chemical Letters, vol. 16, No. 1, pp. 38-40, (2005).
Gao et al. "Affibody-Based Nanoprobes for HER2-Expressing Cell and Tumor Imaging," Biomaterials, vol. 32, pp. 2141-2148, (2010).
Garret et al., "Synthesis and Characterisation of Polyamine-Poly(ethylene glycol) Constructs for DNA Binding and Gene Delivery," Bioorganic & Medicinal Chemistry, vol. 8 pp. 1779-1797, (2000).
Greenwald et al., "Poly(ethylene glycol) Conjugated Drugs and Prodrugs: A Comprehensive Review," Crit. Rev. in Therp. Drug Carr. Sys., vol. 17, No. 2, pp. 101-161, (2000).
Greenwald et al., "Synthesis, Isolation, and Characterization of 2'-Paclitaxel Glycinate: An Application of the Bsmoc Protecting Group," J. Org. Chem., vol. 68, No. 12, pp. 4894-4896, (2003).
Harada et al., "Synthesis of Taxoids II. Synthesis and Antitumor Activity of Water-Soluble Taxoids," Heterocycles, vol. 46, pp. 241-258, (1997).
Harris, Polyethylene Glycol Chemistry: Biotechnical and Biomedical Applications, New York, 11 pages, (1992).
Hodous et al., "Enantioselective Staudinger Synthesis of β-Lactams Catalyzed by a Planar-Chiral Nucleophile," J. Am. Chem. Soc., vol. 124, No. 8, pp. 1578-1579, (2002).
Holton et al., "Selective Protection of the C(7) and C(10) Hydroxyl Groups in 10-Deacetyl Baccatin III," Tetrahedron Letters, vol. 39, pp. 2883-2886, (1998).
Kaliste-Korhonen et al., "Interspecies differences in enzymes reacting with organophosphates and their inhibition by paraoxon in vitro," Hum. & Exp. Toxicol., vol. 15, pp. 972-978, (1996).
Kovtun et al., "Antibody-Maytansinoid Conjugates Designed to Bypass Multidrug Resistance," Cancer Res., vol. 70, No. 6, pp. 2528-2537, (2010).
Kushner et al., "Pharmacological uses and perspectives of heavy water and deuterated compounds," Can. J. Physiol. Pharmacol., vol. 77, pp. 79-88, (1999).
Lee et al., "Catalytic Asymmetric Staudinger Reactions to Form β-Lactams: An Unanticipated Dependence of Diastereoselectivity on the Choice of the Nitrogen Substituent," J. Am. Chem. Soc., vol. 127, No. 33, pp. 11586-11587, (2005).
Lehr, "Antibody-Drug Conjugates > Linker Chemistry," Osage University Partners—Blog, 2 pages, (Feb. 23, 2011).
Li, et al., "Butyrylcholinesterase, paraoxonase, and albumin esterase, but not carboxylesterase, are present in human plasma," Biochem. Pharmacol., vol. 70, pp. 1673-1684, (2005).
Liu et al., "Nano-Sized Assemblies of a PEG-Docetaxel Conjugate as a Formulation Strategy for Docetaxel," J. of Pharma. Sci., vol. 97, No. 8, pp. 3274-3290, (Aug. 2008).
Lu et al., "Synthesis, cytotoxicity, metabolic stability and pharmacokinetic evaluation of fluorinated docetaxel analogs," European Journal of Medicinal Chemistry, vol. 46, pp. 1743-1748, (2011).
Magri et al., "Modified Taxols. 3. Preparation and Acylation of Baccatin III," J. Org. Chem., vol. 51, No. 16, pp. 3239-3242, (1986).
Mahato et al., "Prodrugs for Improving Tumor Targetability and Efficiency," Advanced Drug Delivery Reviews, vol. 63, pp. 659-670, (2011).
Mathew et al., "Synthesis and Evaluation of Some Water-Soluble Prodrugs and Derivatives of Taxol with Antitumor Activity," J. Med. Chem., vol. 35, No. 1, pp. 145-151, (1992).
McPherron et al., "Regulation of Skeletal Muscle Mass in Mice by a New TGF-β Superfamily Member," Nature, vol. 387, pp. 83-90, (1997).
Minagawa et al., "Species Differences in Hydrolysis of Isocarbacyclin Methyl Ester (TEI-9090) by Blood Esterases," Biochem. Pharmacol., vol. 49, No. 10, pp. 1361-1365, (1995).
Ogura et al., "Phase I Study of Inotuzumab Ozogamicin (CMC-544) in Japanese Patients with Follicular Lymphoma Pretreated with Rituximab-based Therapy," Cancer Sci., vol. 101, No. 8, pp. 1840-1845, (2010).
Ojima et al., "Synthesis of New Fluorine-Containing Taxoids by Means of β-Lactam Synthon Method," Tetrahedron, vol. 52, No. 1, pp. 209-224, (1996).
Orlova et al., "Synthetic Affibody Molecules: A Novel Class of Affinity Ligands for Molecular Imaging of HER2-Expressing Malignant Tumors," Cancer Res., vol. 67, pp. 2178-2186, (2007).
Ouchi et al., "Design of Antitumor Agent-Terminated Poly(ethylene Glycol) Conjugate as Macromolecular Prodrug," Polymer Preprints, vol. 38, No. 1, pp. 582-583, (1997).
Pendri et al., "Antitumor activity of paclitaxel-2'-glycinate conjugated to poly(ethylene glycol): a water-soluble prodrug," Anti-Cancer Drug Design, vol. 13, pp. 387-395, (1998).
Pu et al., "Affibody-Attached Hyperbranched Conjugated Polyelectrolyte for Targeted Fluorescence Imaging of HER-Positive Cancer Cell," Biomacromolecules, vol. 12 pp. 2966-2974, (2011).
Pulicani et al., "Direct Access to 2-Debenzoyl Taxoids by Electrochemistry, Synthesis of 2-Modified Docetaxel Analogs," Tetrahedron Letters, vol. 35, No. 52, pp. 9717-9720, (1994).
Quon et al., "Species Differences in the Stereoselective Hydrolysis of Esmolol by Blood Esterases," Drug Metabol. and Disposition, vol. 16, No. 3, pp. 425-428, (1988).
Reimann et al., "A Humanized form of a CD4-Specific Monoclonal Antibody Exhibits Decreased Antigenicity and Prolonged Plasma Half-Life in Rhesus Monkeys While Retaining its Unique Biological and Antiviral Properties," Aids Res. Human Retrovir., vol. 13, pp. 933-943, (1997).
Schuelke et al., "Myostatin Mutation Associated with Gross Muscle Hypertrophy in a Child," New Eng. J. Med., vol. 35, pp. 2682-2688, (2007).
Serrano-Wu et al., "Mild deprotection of 2-(trimethylsilyl)ethyl esters," Tetrahedron Letters, vol. 42, pp. 8593-8595, (2001).
Spiridon et al., "Targeting Multiple Her-2 Epitopes with Monoclonal Antibodies Results in Improved Antigrowth Activity of a Human Breast Cancer Cell Lind in Vitro and in Vivo," Clinical Cancer Research, vol. 8, No. 6, pp. 1720-1730, (2002).
Sugahara et al., "Paclitaxel Delivery Systems: The Use of Amino Acid Linkers in the Conjugation of Paclitaxel with Carboxymethyldextran to Create Prodrugs," Biol. Pharm. Bull., vol. 25, No. 5, pp. 632-641, (2002).
Tai et al., "The Role of HER2 in Cancer Therapy and Targeted Drug Delivery," J. of Controlled Release, Elsevier, Amsterdam, vol. 146, No. 3, pp. 264-275, (2010).

(56) References Cited

OTHER PUBLICATIONS

Van Vlerken et al., "Poly(ethylene glycol)-modified Nanocarriers for Tumor-targeted and Intracellular Delivery," Pharmaceutical Research, 10 pages, (2007).
Veronese, "Peptide and protein PEGylation: a review of problems and solutions," Biomaterials, vol. 22, pp. 405-417, (2001).
Warnecke et al., "Maleimide-oligo(ethylene glycol) Derivatives of Camptothecin as Albumin-Binding Prodrugs: Synthesis and Antitumor Efficacy," Bioconj. Chem., vol. 14, pp. 377-387, (2003).
Williams, "Clinical Significance of Esterases in Man," Clin. Pharmacokin., vol. 10, pp. 392-403, (1985).
Wittman et al., "Synthesis of Metabolically Blocked Paclitaxel Analogues," Bioorganic & Medicinal Chemistry Letters, vol. 11, pp. 809-810, (2001).
Xiao, et al., "Design and Synthesis of a Taxoid Library Using Radiofrequency Encoded Combinatorial Chemistry," J. Org. Chem., vol. 62, No. 17, pp. 6029-6033, (1997).
Zalipsky, "Chemistry of Polyethylene Glycol Conjugates with Biologically Active Molecules," Advanced Drug Reviews, vol. 16, pp. 157-182, (1995).
Zalipsky et al., "Polyethylene Glycol Chemistry: Biotechnical and Biomedical Applications: Use of Functionalized Poly(Ethylene Glycols) for Modification of Polypeptide," New York, 13 pages, (1992).
Zhang et al., "Chiral N-Heterocyclic Carbene Catalzyed Staudinger Reaction of Ketenes with Imines: Highly Enantioselective Synthesis of N-Boc β-Lactams," Organic Letters, vol. 10, No. 2, pp. 277-280, (2008).
Zimmers et al., "Induction of Cachexia in Mice by Systemically Administered Myostatin," Science, vol. 296, pp. 1486-1488, (2002).
PCT International Search Report and Written Opinion corresponding to PCT Application No. PCT/US2009/004618 dated Dec. 29, 2009.
PCT International Preliminary Report on Patentability corresponding to PCT Application No. PCT/US2009/004618 dated Feb. 24, 2011.
PCT International Search Report and Written Opinion corresponding to PCT International Application No. PCT/US2011/066909 dated Apr. 5, 2012.
PCT International Preliminary Report on Patentability corresponding to PCT International Application No. PCT/US2011/066909 dated Jul. 4, 2013.
PCT International Search Report and Written Opinion corresponding to PCT International Application No. PCT/US2011/066778 dated Apr. 3, 2012.
PCT International Preliminary Report on Patentability corresponding to PCT International Application No. PCT/US2011/066778 dated Jul. 4, 2013.
PCT International Search Report and Written Opinion corresponding to PCT Application No. PCT/US2011/066876 dated Mar. 14, 2012.
PCT International Preliminary Report on Patentability corresponding to PCT Application No. PCT/US2011/066876 dated Jul. 4, 2013.
PCT International Search Report and Written Opinion corresponding to PCT Application No. PCT/US2012/039453 dated Aug. 8, 2012.
PCT International Preliminary Report on Patentability corresponding to PCT Application No. PCT/2012/039453 dated Dec. 12, 2013.
Australian Patent Examination Report No. 1 in Australian Patent Application No. 2009282413 dated Jun. 14, 2013.
Canadian Office Action in Canadian Patent Application No. 2,732,508 dated Mar. 18, 2015.
English Translation of Notification of the First Office Action in Chinese Patent Application No. 200980136289.7 dated Mar. 26, 2012.
English Translation of Notification of the Second Office Action in Chinese Patent Application No. 200980136289.7 dated Feb. 1, 2013.
English Translation of Notification of the Third Office Action in Chinese Patent Application No. 200980136289.7 dated Nov. 1, 2013.
European Communication in European Patent Application No. 09 789 119.6-1216 dated Nov. 4, 2011.
English Translation of First Substantive Examination Report in Israel Patent Application No. 211,180 dated Feb. 3, 2014.
English Translation of Office Communication into Israeli Patent Application No. 211,180 dated Oct. 13, 2015.
English Translation of Notice of Reasons for Rejection in Japanese Patent Application No. 2011-522993 dated Oct. 18, 2013.
English Translation of Notice of Reasons for Rejection in Japanese Patent Application No. 2011-522993 dated Feb. 4, 2014.
English Translation of Notice of Grounds for Rejection in Korean Patent Application No. 2011-7004008 dated Jul. 14, 2015.
English Translation of Communication of the Substantive Examination Report in Mexican Patent Application No. MX/a/2011/001583 dated Mar. 5, 2014.
Crown et al., "Docetaxel and Paclitaxel in the Treatment of Breast Cancer: A Review of Clinical Experience", The Oncologist, vol. 9, Suppl. 2, pp. 24-32, (2004).

* cited by examiner

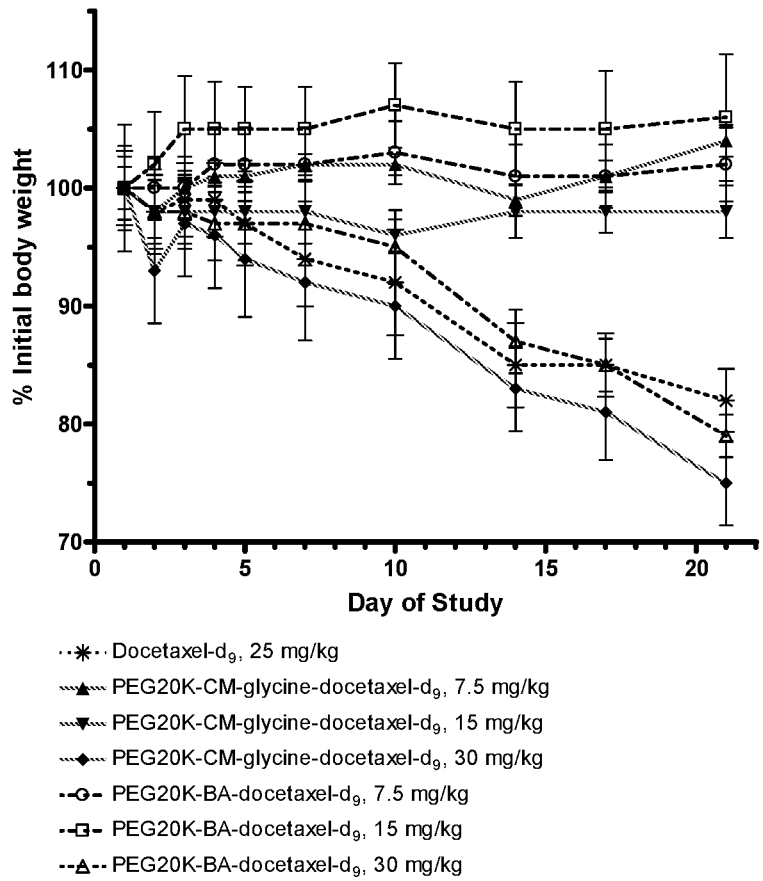

- ··✱·· Docetaxel-d$_9$, 25 mg/kg
- ▲ PEG20K-CM-glycine-docetaxel-d$_9$, 7.5 mg/kg
- ▼ PEG20K-CM-glycine-docetaxel-d$_9$, 15 mg/kg
- ◆ PEG20K-CM-glycine-docetaxel-d$_9$, 30 mg/kg
- -○- PEG20K-BA-docetaxel-d$_9$, 7.5 mg/kg
- -□- PEG20K-BA-docetaxel-d$_9$, 15 mg/kg
- -△- PEG20K-BA-docetaxel-d$_9$, 30 mg/kg where "PEG20K-CM-glycine-docetaxel-d$_9$" corresponds to 4-ARM-PEG$_{20K}$-Glycinate-Linked d$_9$-Docetaxel Conjugate ("4-ARM-PEG$_{20K}$-CM-GLY-d$_9$-DOC") (Example 16)

and where "PEG20K-BA-docetaxel-d$_9$ corresponds to 4-ARM-PEG$_{20K}$-Butanoate-Linked d$_9$-Docetaxel Conjugate ("4-ARM-PEG$_{20K}$-BA-D$_9$-DOC") (Example 17)

MULTI-ARM POLYMERIC PRODRUG CONJUGATES OF TAXANE-BASED COMPOUNDS

CROSS-REFERENCE TO RELATED APPLICATIONS

This application is a continuation of U.S. patent application Ser. No. 13/995,287, filed on 27 Aug. 2013, which is a 35 U.S.C. § 371 application of International Application No. PCT/US2011/066853, filed on 22 Dec. 2011, which claims the benefit of priority under 35 U.S.C. § 119(e) to U.S. Provisional Patent Application Ser. No. 61/426,227, filed on Dec. 22, 2010, the disclosures of which are incorporated herein by reference in their entirety.

FIELD

This disclosure relates generally to conjugates of docetaxel- and cabazitaxel-based compounds (e.g., deuterated and/or fluorinated forms of docetaxel and cabazitaxel) to a multi-arm, water-soluble polymer. The linkage between the docetaxel- and cabazitaxel-based compound and the multi-arm, water-soluble polymer is releasable, thereby enabling release of the docetaxel- and cabazitaxel-based compound following administration of the conjugate to a patient. The invention relates to and/or has application(s) in (among others) the fields of drug discovery, pharmacotherapy, physiology, organic chemistry and polymer chemistry.

BACKGROUND

Over the years, numerous methods have been proposed for improving the delivery of biologically active agents, particularly small molecule drugs. Challenges associated with the formulation and delivery of pharmaceutical agents can include poor aqueous solubility of the pharmaceutical agent, toxicity, low bioavailability, instability, and rapid in-vivo degradation. Although many approaches have been devised for improving the delivery of pharmaceutical agents, no single approach is without its drawbacks. For instance, commonly employed drug delivery approaches aimed at solving or at least ameliorating one or more of these challenges include drug encapsulation (such as in a liposome, polymer matrix, or unimolecular micelle), covalent attachment to a water-soluble polymer (i.e., conjugation) such as polyethylene glycol (i.e., PEG or PEGylation), use of gene targeting agents, and the like.

PEGylation has been employed to improve the bioavailability and ease of formulation of small molecule therapeutics having poor aqueous solubilities. For instance, water-soluble polymers such as PEG have been covalently attached to artilinic acid to improve its aqueous solubility. See U.S. Pat. No. 6,461,603. Similarly, PEG has been covalently attached to triazine-based compounds such as trimelamol to improve their solubility in water and enhance their chemical stability. See International Patent Application Publication No. WO 02/043772. Covalent attachment of PEG to bisindolyl maleimides has been employed to improve poor bioavailability of such compounds due to low aqueous solubility. See International Patent Application Publication No. WO 03/037384. Polymer conjugates of non-steroidal anti-inflammatory drugs (NSAIDs) and of opioid antagonists have also been prepared. See U.S. Patent Application Publication Nos. 2007/0025956 and 2006/0105046, respectively. Prodrugs of camptothecin having one or two molecules of camptothecin covalently attached to a linear polyethylene glycol have also been prepared. See U.S. Pat. No. 5,880,131. Prodrugs of irinotecan and docetaxel having (among other things) four molecules of drug covalently attached to a multi-arm polymer have been described in U.S. Pat. No. 7,744,861 and International Patent Application Publication No. WO 10/019233, respectively.

Certain drugs, such as the alkaloids, are notoriously difficult to solubilize. Such alkaloids include the taxanes. Cabazitaxel is a drug within the taxane class of anti-cancer agents that is approved in combination with prednisone for the treatment of individuals suffering from hormone-refractory metastatic prostate cancer who are were previously treated with a docetaxel-containing treatment regimen.

The chemical name of cabazitaxel is (2α,5β,7β,10β,13α)-4-acetoxy-13-({(2R,3S)-3-[(tertbutoxycarbonyl)amino]-2-hydroxy-3-phenylpropanoyl}oxy)-1-hydroxy-7,10-dimethoxy-9-oxo-5,20-epoxytax-11-en-2-yl benzoate, which has the following chemical structure:

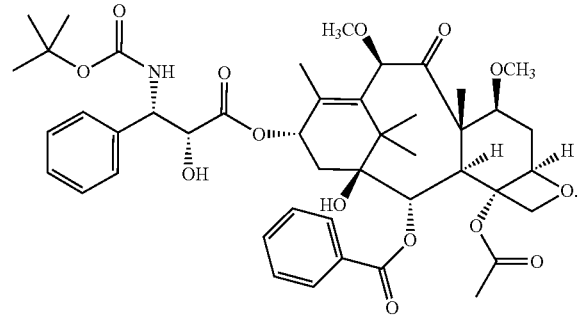

Commercially, cabazitaxel is available as the acetone solvate under the JEVTANA® brand from Sanofi-aventis (Bridgewater, N.J.). This commercially available form also includes Polysorbate 80 as a solubilizing agent for the drug.

Although shown to provide several advantages over other taxanes (such as docetaxel) for certain indications, cabazitaxel is also associated with drawbacks as well. For example, cabazitaxel has a toxicity profile that is similar to docetaxel and is believed to be dependent on both the rate of drug clearance from the body as well as the patient's cytochrome CYP3A4 metabolic activity. In this regard, patients given a standard dose of cabazitaxel exhibit a wide interpatient variation in clearance and toxic effects, thereby supporting the concept that interpatient differences in metabolic activity accounts for at least some of this variance.

In addition, administration of cabazitaxel and other conventional taxane-based therapeutics may not distribute to the desired areas in vivo. In this regard, these conventional molecules may distribute relatively evenly throughout a patient's body, thereby exerting their effects on both normal and cancerous tissues. It would be desirous, however, if cabazitaxel and other conventional taxane-based could be modified in such a way so as to accumulate in tumor tissues while still retaining their potent anti-cancer effects.

The present invention seeks to address these and/or other needs.

SUMMARY

In one or more embodiments of the invention, conjugates are provided, the conjugates having a structure encompassed by the formula:

Formula I

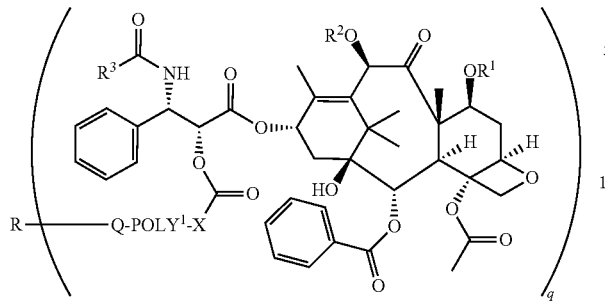

wherein:

R is a residue of a polyol, polythiol or polyamine bearing from 3 to about 50 hydroxyl, thiol or amino groups;

each Q is a linker (and, in one or more embodiments, a hydrolytically stable linker);

each $POLY^1$ is a water-soluble, non-peptidic polymer;

each X is spacer moiety that optionally includes a releasable linkage (e.g., a hydrolyzable linkage, an enzymatically degradable linkage, and so forth);

each $R^1$ is selected from the group consisting of H, a hydroxy protecting group and

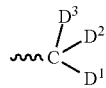

and each of $D^1$, $D^2$ and $D^3$ is independently selected from the group consisting of H, F, D and $CF_3$ (in one or more embodiments, $R^1$ is either a hydroxy protecting group or

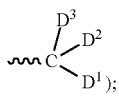
);

each $R^2$ is selected from the group consisting of H, a hydroxy protecting group and

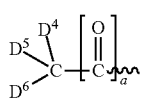

and (a) is either zero or one and each of $D^4$, $D^5$ and $D^6$ is independently selected from the group consisting of H, F, D and $CF_3$ (in one or more embodiments, $R^2$ is either a hydroxy protecting group or

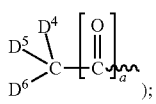
);

each $R^3$ is

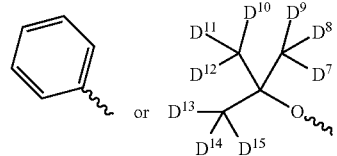

and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$; and q is a positive integer from 3 to about 50 (e.g., 4), and pharmaceutically acceptable salts and solvates thereof.

In one or more embodiments, when the conjugates encompassed by Formula I have hydrogens at each of $R^1$ and $R^2$, $R^3$ is

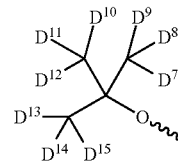

with at least one of $D^7$, $D^8$, $D^9$, $D^{10}$, $D^{11}$, $D^{12}$, $D^{13}$, $D^{14}$ and $D^{15}$ defined as F, D or $CF_3$.

In one or more embodiments of the invention, a conjugate-containing composition is provided, the conjugate-containing composition comprising four-arm conjugates, wherein at least 80% of the four-arm conjugates in the composition have a structure encompassed by the formula,

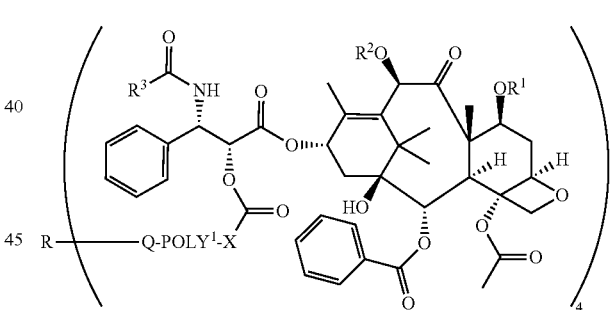

wherein:

R is a residue of a polyol, polythiol or polyamine bearing from 3 to about 50 hydroxyl, thiol or amino groups;

each Q is a linker (and, in one or more embodiments, a hydrolytically stable linker);

each $POLY^1$ is a water-soluble, non-peptidic polymer;

each X is spacer moiety that optionally includes a releasable linkage (e.g., a hydrolyzable linkage, an enzymatically degradable linkage, and so forth);

each $R^1$ is selected from the group consisting of H, a hydroxy protecting group and

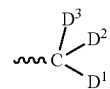

and each of $D^1$, $D^2$ and $D^3$ is independently selected from the group consisting of H, F, D and $CF_3$ (in one or more embodiments, $R^1$ is either a hydroxy protecting group or

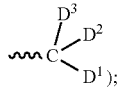

each $R^2$ is selected from the group consisting of H, a hydroxy protecting group and

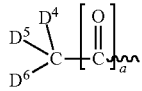

and (a) is either zero or one and each of $D^4$, $D^5$ and $D^6$ is independently selected from the group consisting of H, F, D and $CF_3$ (in one or more embodiments, $R^2$ is either a hydroxy protecting group or

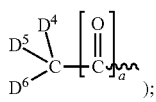

each $R^3$ is

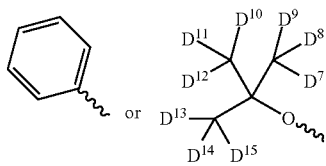

and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$; and q is a positive integer from 3 to about 50 (e.g., 4), and pharmaceutically acceptable salts and solvates thereof.

In one or more embodiments, when the conjugates encompassed by the formula set forth in this paragraph have hydrogens at each of $R^1$ and $R^2$, $R^3$ is

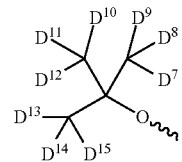

with at least one of $D^7$, $D^8$, $D^9$, $D^{10}$, $D^{11}$, $D^{12}$, $D^{13}$, $D^{14}$ and $D^{15}$ defined as F, D or $CF_3$.

In one or more embodiments of the invention, conjugates are provided, the conjugates having a structure encompassed by the formula:

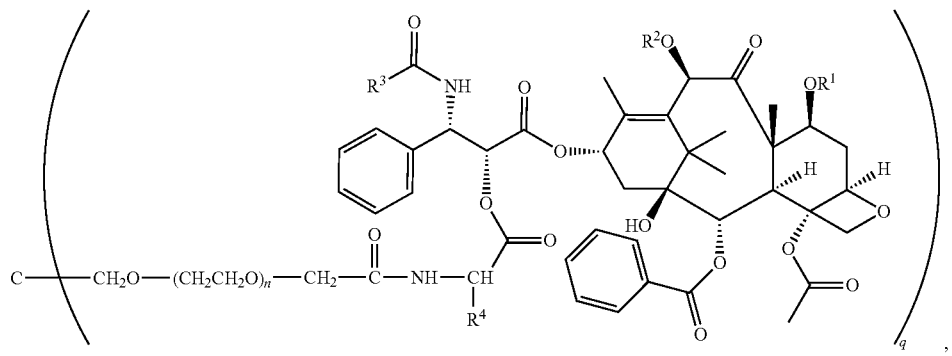

wherein:
each n is a positive integer from 10 to about 400;
each $R^1$ is selected from the group consisting of H, a hydroxy protecting group and

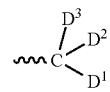

and each of $D^1$, $D^2$ and $D^3$ is independently selected from the group consisting of H, F, D and $CF_3$ (in one or more embodiments, $R^1$ is either a hydroxy protecting group or

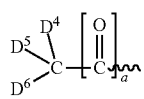

each $R^2$ is selected from the group consisting of H, a hydroxy protecting group and

and (a) is either zero or one and each of $D^4$, $D^5$ and $D^6$ is independently selected from the group consisting of H, F, D and $CF_3$ (in one or more embodiments, $R^2$ is either a hydroxy protecting group or $$D^5 \underset{D^6}{\overset{D^4}{\diagdown}} C \!-\!\!\left[ \overset{\overset{O}{\|}}{C} \right]_a \!\!\sim\!);$$

each R³ is

<chemical structure: phenyl-CH~ or D¹³(D¹⁴)(D¹⁵)C-C(D¹²)(D¹¹)-C(D⁷)(D⁸)(D⁹⁻ᴰ¹⁰)... O~ > and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$;

$R^4$ is selected from the group consisting of H, $CH_3$, $CH(CH_3)_2$, $CH_2CH(CH_3)_2$ and $C(H)(CH_3)CH_2CH_3$; and q is a positive integer from 3 to about 50 (e.g., 4), and pharmaceutically acceptable salts and solvates thereof. In one or more embodiments, when the conjugates encompassed by the formula set forth in this paragraph have hydrogens at each of $R^1$ and $R^2$, $R^3$ is <chemical structure> with at least one of $D^7$, $D^8$, $D^9$, $D^{10}$, $D^{11}$, $D^{12}$, $D^{13}$, $D^{14}$ and $D^{15}$ defined as F, D or $CF_3$.

In one or more embodiments of the invention, conjugates are provided, the conjugates having a structure encompassed by the following formula:

<chemical structure of taxane-PEG conjugate> wherein:
each n is a positive integer from 10 to about 400;
each m is a positive integer from 1 to about 12;
each $R^1$ is selected from the group consisting of H, a hydroxy protecting group and <chemical structure: C(D¹)(D²)(D³)> and each of $D^1$, $D^2$ and $D^3$ is independently selected from the group consisting of H, F, D and $CF_3$ (in one or more embodiments, $R^1$ is either a hydroxy protecting group or <chemical structure: C(D¹)(D²)(D³)>);

each $R^2$ is selected from the group consisting of H, a hydroxy protecting group and $$D^5 \underset{D^6}{\overset{D^4}{\diagdown}} C \!-\!\!\left( \overset{\overset{O}{\|}}{C} \right)_{\!\!a} \!\!\sim$$

and (a) is either zero or one and each of $D^4$, $D^5$ and $D^6$ is independently selected from the group consisting of H, F, D and $CF_3$ (in one or more embodiments, $R^2$ is either a hydroxy protecting group or $$D^5 \underset{D^6}{\overset{D^4}{\diagdown}} C \!-\!\!\left( \overset{\overset{O}{\|}}{C} \right)_{\!\!a} \!\!\sim \!);$$

each $R^3$ is

<chemical structure: phenyl or tBu-like group with D labels> and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$; and q is a positive integer from 3 to about 50 (e.g., 4), and pharmaceutically acceptable salts and solvates thereof. In one or more embodiments, when the conjugates encompassed by the formula set forth in this paragraph have hydrogens at each of $R^1$ and $R^2$, $R^3$ is

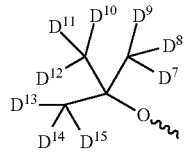

with at least one of $D^7$, $D^8$, $D^9$, $D^{10}$, $D^{11}$, $D^{12}$, $D^{13}$, $D^{14}$ and $D^{15}$ defined is F, D or $CF_3$.

In one or more embodiments of the invention, conjugates are provided, the conjugates having a structure encompassed by the following formula:

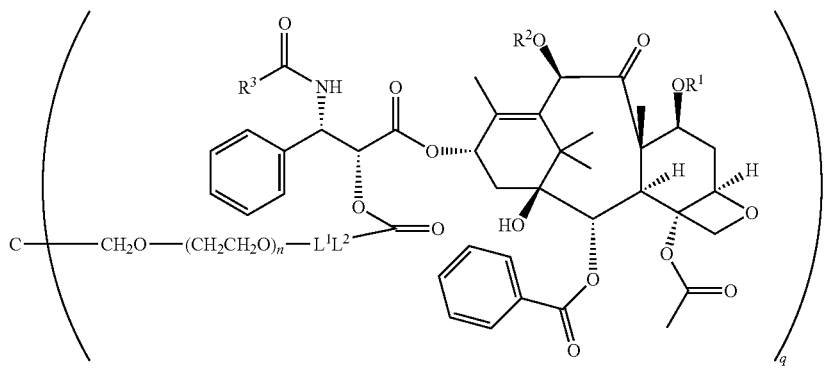

wherein:

each n is a positive integer from 10 to about 400;

each $L^1$ is —$(CH_2)_{0-6}C(=O)$— (for clarity, the carbonyl carbon is proximal to $L^2$);

each $L^2$ is —$NH(CH_2CH_2O)_{1-10}(CHR^5)_{1-6}$—, wherein each $R^5$ is independently selected from the group consisting of H and lower alkyl (e.g., $CH_3$) (for clarity, the nitrogen is proximal to $L^1$);

each $R^1$ is selected from the group consisting of H, a hydroxy protecting group and

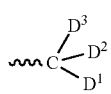

and each of $D^1$, $D^2$ and $D^3$ is independently selected from the group consisting of H, F, D and $CF_3$ (in one or more embodiments, $R^1$ is either a hydroxy protecting group or

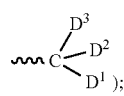

);

each $R^2$ is selected from the group consisting of H, a hydroxy protecting group and

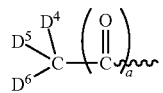

and (a) is either zero or one and each of $D^4$, $D^5$ and $D^6$ is independently selected from the group consisting of H, F, D and $CF_3$ (in one or more embodiments, $R^2$ is either a hydroxy protecting group or

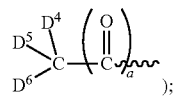

);

each $R^3$ is

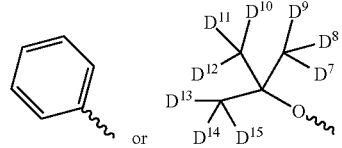

and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$; and q is a positive integer from 3 to about 50 (e.g., 4), and pharmaceutically acceptable salts and solvates thereof. In one or more embodiments, when the conjugates encompassed by the formula set forth in this paragraph have hydrogens at each of $R^1$ and $R^2$, $R^3$ is

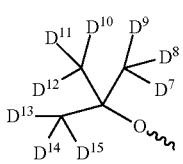

with at least one of $D^7$, $D^8$, $D^9$, $D^{10}$, $D^{11}$, $D^{12}$, $D^{13}$, $D^{14}$ and $D^{15}$ defined as F, D or $CF_3$.

In one or more embodiments of the invention, conjugates are provided, the conjugates having a structure encompassed by the following formula:

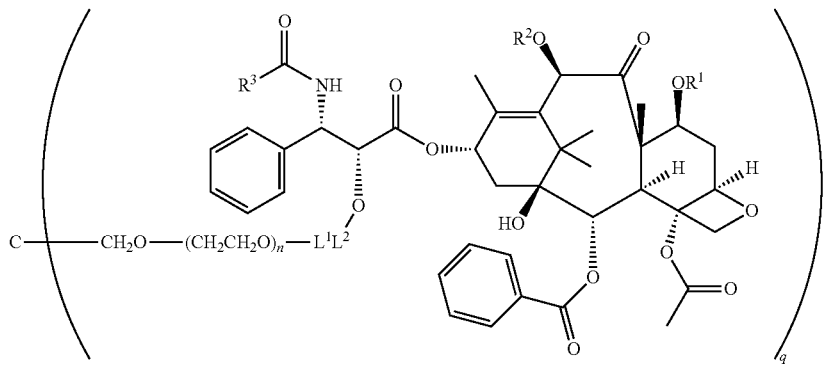

wherein:

each n is a positive integer from 10 to about 400;

each $L^1$ is —$(CH_2)_{0-6}C(=O)$— (for clarity, the carbonyl carbon is proximal to $L^3$);

each $L^3$ is —$[NH(CHR^5)_{1-6}C(=O)]_{1-4}$—, wherein each $R^5$ is independently selected from the group consisting of H and lower alkyl (e.g., $CH_3$) (for clarity, the nitrogen is proximal to $L^1$);

each $R^1$ is selected from the group consisting of H, a hydroxy protecting group and

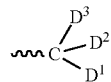

and each of $D^1$, $D^2$ and $D^3$ is independently selected from the group consisting of H, F, D and $CF_3$ (in one or more embodiments, $R^1$ is either a hydroxy protecting group or

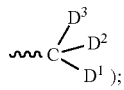

each $R^2$ is selected from the group consisting of H, a hydroxy protecting group and

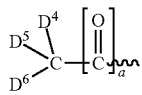

and (a) is either zero or one and each of $D^4$, $D^5$ and $D^6$ is independently selected from the group consisting of H, F, D and $CF_3$ (in one or more embodiments, $R^2$ is either a hydroxy protecting group or

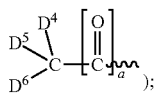

each $R^3$ is

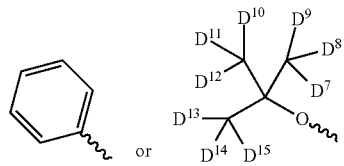

and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$; and q is a positive integer from 3 to about 50 (e.g., 4), and pharmaceutically acceptable salts and solvates thereof.

In one or more embodiments, when the conjugates encompassed by the formula set forth in this paragraph have hydrogens at each of $R^1$ and $R^2$, $R^3$ is

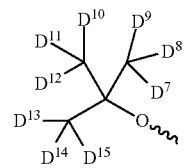

with at least one of $D^7$, $D^8$, $D^9$, $D^{10}$, $D^{11}$, $D^{12}$, $D^{13}$, $D^{14}$ and $D^{15}$ defined as F, D or $CF_3$.

In one or more embodiments of the invention, a pharmaceutical composition is provided, the pharmaceutical composition comprising a conjugate as described herein and a pharmaceutically acceptable carrier.

In one or more embodiments of the invention, a method is provided, the method comprising administering a conjugate as described herein (preferably in a pharmaceutical composition containing a pharmaceutically acceptable amount of the conjugate) to an individual.

In one or more embodiments of the invention, a method is provided, the method comprising a multi-arm water-soluble, non-peptidic polymer structure having "q" polymer arms, each individual polymer arm having a reactive carbonate, carboxylic acid group or activated ester thereof at its terminus, with "q" moles or greater of a compound having the following structure:

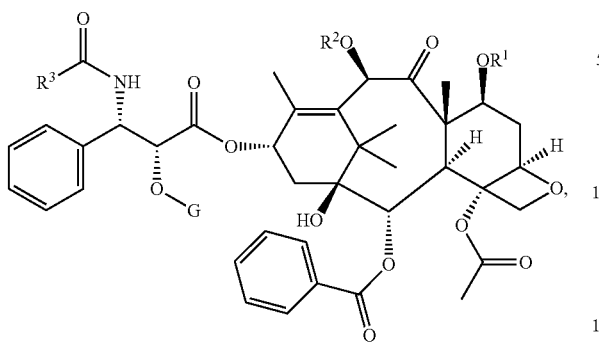
(Formula II)

wherein:

G is either H or –C(O)—(CHR$^6$)$_{1-6}$—NH$_2$, wherein each R$^6$ is independently selected from the group consisting of H, lower alkyl and arylalkyl, and optionally, when G is –C(O)—(CHR$^6$)$_{1-6}$—NH$_2$, the NH$_2$ group is protected;

R$^1$ is selected from the group consisting of H, a hydroxy protecting group and

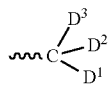

and each of D$^1$, D$^2$ and D$^3$ is independently selected from the group consisting of H, F, D and CF$_3$ (in one or more embodiments, R$^1$ is either a hydroxyl protecting group or

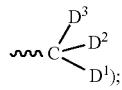
);

R$^2$ is selected from the group consisting of H, a hydroxy protecting group and

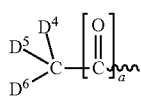

and (a) is either zero or one and each of D$^4$, D$^5$ and D$^6$ is independently selected from the group consisting of H, F, D and CF$_3$ (in one or more embodiments, R$^2$ is either a hydroxyl protecting group or

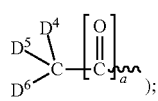
);

R$^3$ is

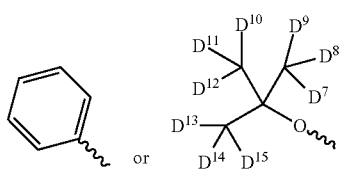

and each of D$^7$, D$^8$, D$^9$, D$^{10}$, D$^{11}$, D$^{12}$, D$^{13}$, D$^{14}$ and D$^{15}$ is independently selected from the group consisting of H, F, D and CF$_3$. In one or more embodiments, when the compound used in accordance with the method set forth in this paragraph have hydrogens at each of R$^1$ and R$^2$, R$^3$ is

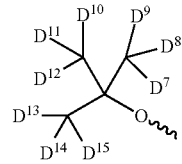

with at least one of D$^7$, D$^8$, D$^9$, D$^{10}$, D$^{11}$, D$^{12}$, D$^{13}$, D$^{14}$ and D$^{15}$ defined as F, D or CF$_3$.

Additional embodiments of the present conjugates, compositions, methods, and the like will be apparent from the description that follows. Additional aspects and advantages of the present invention are set forth in the following description and claims, particularly when considered in conjunction with the accompanying examples and drawings.

BRIEF DESCRIPTION OF THE DRAWING

FIG. 1 is a plot showing the body weight changes (based on percent) of athymic mice following administration of d$_9$-docetaxel or 4-arm-PEG20K conjugates of d$_9$-docetaxel, as further described in Example 3.

DETAILED DESCRIPTION

Various aspects of the invention now will be described more fully hereinafter. Such aspects may, however, be embodied in many different forms and should not be construed as limited to the embodiments set forth herein; rather, these embodiments are provided so that this disclosure will be thorough and complete, and will fully convey the scope of the invention to those skilled in the art.

Definitions

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

A "functional group" is a group that may be used, under normal conditions of organic synthesis, to form a covalent linkage between the entity to which it is attached and another entity, which typically bears a further functional group. The functional group generally includes multiple bond(s) and/or heteroatom(s). Preferred functional groups for use in the polymers of the invention are described below.

The term "reactive" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive", with reference to a functional group present on a molecule in a reaction mixture, indicates that the group remains largely intact under conditions effective to produce a desired reaction in the reaction mixture.

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include, for example, imidazolyl esters, and benzotriazole esters, and imide esters, such as N-hydroxysuccinimidyl (NHS) esters. An activated derivative may be formed in situ by reaction of a carboxylic acid with one of various reagents, e.g., benzotriazol-1-yloxy tripyrrolidinophosphonium hexafluorophosphate (PyBOP), preferably used in combination with 1-hydroxy benzotriazole (HOBT) or 1-hydroxy-7-azabenzotriazole (HOAT); O-(7-azabenzotriazol-1-yl)-N,N,N',N'-tetramethyluronium hexafluorophosphate (HATU); or bis(2-oxo-3-oxazolidinyl) phosphinic chloride (BOP-Cl).

A "chemical equivalent" of a functional group is one that possesses essentially the same type of reactivity as the functional group. For instance, one functional group that undergoes an SN2 reaction is considered to be a functional equivalent of another such functional group.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups that may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and in P. J. Kocienski, *Protecting Groups*, Third Ed., Thieme Chemistry, 2003, and references cited therein.

A functional group in "protected form" refers to a functional group bearing a protecting group. As used herein, the term "functional group" or any synonym thereof is meant to encompass protected forms thereof.

"PEG" or "poly(ethylene glycol)" as used herein, is meant to encompass any water-soluble poly(ethylene oxide). Typically, PEGs for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation, or, e.g., the identity of adjacent functional groups. The variable (n) typically ranges from 3 to about 3000, and the terminal groups and architecture of the overall PEG may vary. When PEG or a conjugate comprising a PEG segment further comprises a spacer or a linker as in Compound I above (to be described in greater detail below), the atoms comprising the spacer (X) or linker (Q), when covalently attached to a PEG segment, do not result in formation of (i) an oxygen-oxygen bond (—O—O—, a peroxide linkage), or (ii) a nitrogen-oxygen bond (N—O, O—N). PEGs for use in the invention include PEGs having a variety of molecular weights, structures or geometries to be described in greater detail below.

"Water-soluble," in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

"Non-naturally occurring" with respect to a polymer means a polymer that in its entirety is not found in nature. A non-naturally occurring polymer may however contain one or more subunits or segments of subunits that are naturally occurring, so long as the overall polymer structure is not found in nature.

"Molecular mass" in the context of a water-soluble polymer such as PEG, refers to the nominal average molecular mass of a polymer, typically determined by size exclusion chromatography, light scattering techniques, or intrinsic viscosity determination in water or organic solvents. Molecular weight in the context of a water-soluble polymer, such as PEG, can be expressed as either a number-average molecular weight or a weight-average molecular weight. Unless otherwise indicated, all references to molecular weight herein refer to the number-average molecular weight. Both molecular weight determinations, number-average and weight-average, can be measured using gel permeation chromatographic techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 1.2, less than about 1.15, less than about 1.10, less than about 1.05, and less than about 1.03. As used herein, references will at times be made to a single water-soluble polymer having either a weight-average molecular weight or number-average molecular weight; such references will be understood to mean that the single-water soluble polymer was obtained from a composition of water-soluble polymers having the stated molecular weight.

The term "linker" is used herein to refer to an atom or a collection of atoms used to link interconnecting moieties, such as an organic radical core and a polymer segment, POLY$^1$. A linker moiety may be hydrolytically stable or may include a releasable linkage (e.g., a physiologically hydrolysable linkage, an enzymatically degradable linkage, or another linkage that cleaves in vivo).

The term "spacer" is used herein to refer to an atom or a collection of atoms used to link interconnecting moieties, such as POLY$^1$ and a drug. A spacer moiety may be hydrolytically stable or may include a physiologically hydrolyzable or enzymatically degradable linkage.

A "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Illustrative hydrolytically unstable linkages include carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes. Such a linkage requires the action of one or more enzymes to effect degradation.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multi-armed" in reference to the geometry or overall structure of a polymer refers to polymer having 3 or more polymer-containing "arms" connected to a "core" molecule or structure. Thus, a multi-armed polymer may possess 3 polymer arms, 4 polymer arms, 5 polymer arms, 6 polymer arms, 7 polymer arms, 8 polymer arms or more, depending upon its configuration and core structure. One particular type of highly branched polymer is a dendritic polymer or dendrimer, that, for the purposes of the invention, is considered to possess a structure distinct from that of a multi-armed polymer. That is to say, a multi-armed polymer as referred to herein explicitly excludes dendrimers. Additionally, a multi-armed polymer as provided herein possesses a non-crosslinked core.

A "dendrimer" is a globular, size monodisperse polymer in which all bonds emerge radially from a central focal point or core with a regular branching pattern and with repeat units that each contribute a branch point. Dendrimers are typically formed using a nano-scale, multistep fabrication process. Each step results in a new "generation" that has two or more times the complexity of the previous generation. Dendrimers exhibit certain dendritic state properties such as core encapsulation, making them unique from other types of polymers.

"Branch point" refers to a bifurcation point comprising one or more atoms at which a polymer splits or branches from a linear structure into one or more additional polymer arms. A multi-arm polymer may have one branch point or multiple branch points, so long as the branches are not regular repeats resulting in a dendrimer.

"Substantially" or "essentially" means nearly totally or completely, for instance, 95% or greater of some given quantity.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, isopropyl, n-butyl, n-pentyl, 2-methyl-1-butyl, 3-pentyl, 3-methyl-3-pentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

As used herein, "alkenyl" refers to a branched or unbranched hydrocarbon group of 1 to 15 atoms in length, containing at least one double bond, such as ethenyl (vinyl), 2-propen-1-yl (allyl), isopropenyl, 3-buten-1-yl, and the like.

The term "alkynyl" as used herein refers to a branched or unbranched hydrocarbon group of 2 to 15 atoms in length, containing at least one triple bond, ethynyl, 1-propynyl, 3-butyn-1-yl, 1-octyn-1-yl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein includes any agent, drug, compound, and the like which provides some pharmacologic, often beneficial, effect that can be demonstrated in vivo or in vitro. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in a target tissue or site in the body. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multi-functional" in the context of a polymer of the invention means a polymer having 3 or more functional groups, where the functional groups may be the same or different, and are typically present on the polymer termini. Multi-functional polymers of the invention will typically contain from about 3-100 functional groups, or from 3-50 functional groups, or from 3-25 functional groups, or from 3-15 functional groups, or from 3 to 10 functional groups, i.e., contains 3, 4, 5, 6, 7, 8, 9 or 10 functional groups. Typically, in reference to a polymer precursor used to prepare a polymer conjugate of the invention, the polymer possesses 3 or more polymer arms having at the terminus of each arm a functional group suitable for coupling to an active agent moiety via a hydrolyzable ester linkage. Typically, such functional groups are the same.

A basic or acidic reactant described herein includes neutral, charged, and any corresponding salt forms thereof.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer may include a minor number of peptide linkages spaced along the repeat monomer subunits, such as, for example, no more than about 1 peptide linkage per about 50 monomer units.

The terms "subject," "individual" or "patient" are used interchangeably herein and refer to a vertebrate, preferably a mammal. Mammals include, but are not limited to, murines, rodents, simians, humans, farm animals, sport animals and pets. Such subjects are typically suffering from or prone to a condition that can be prevented or treated by administration of a polymer of the invention, typically but not necessarily in the form of a polymer-active agent conjugate as described herein.

"Treatment" or "treating" of a particular condition includes: (1) preventing such a condition, i.e., causing the condition not to develop, or to occur with less intensity or to a lesser degree in a subject that may be exposed to or predisposed to the condition but does not yet experience or display the condition; and/or (2) inhibiting the condition, i.e., arresting the development or reversing the condition.

"Optional" or "optionally" means that the subsequently described circumstance may or may not occur, so that the description includes instances where the circumstance occurs and instances where it does not.

A "residue" refers to a portion of compound remaining or present following a chemical reaction (whether a synthetic chemical reaction or following compound releasing-chemical reaction). For example, a polyol that is used to form a multi-arm polymer will have a "residue" of that polyol present in the multi-arm polymer.

A "polyol" is an alcohol containing more than two hydroxyl groups, where the prefix "poly" in this instance refers to a plurality of a certain feature rather than to a polymeric structure. Similarly, a polythiol is a thiol containing more than two thiol (—SH) groups, and a polyamine is an amine containing more than two amino groups.

As previously indicated, one or more embodiments of the invention relate to conjugates having a structure encompassed by Formula I. The conjugates of the invention are both prodrugs and "multi-armed." Thus, upon administration to an individual, the prodrug releases in vivo a compound lacking attachment to the water-soluble, non-peptidic polymer via in vivo cleavage. For example, in vivo cleavage of an ester may occur with or without the benefit of an esterase. In an additional example, in vivo cleavage of an amide may occur with the benefit of, for example, a peptidase (such as a γ-glutamyl hydrolase). Because the conjugates are multi-armed, release occurs multiple times, thereby delivering following administration several moles of released compound for each mole of starting conjugate.

Thus, exemplary conjugates of the invention have a structure encompassed by the formula:

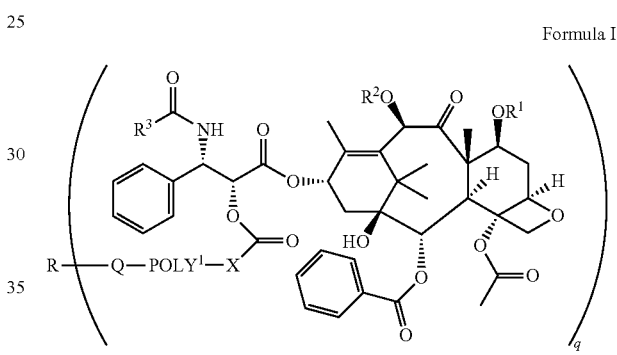

Formula I wherein:
R is a residue of a polyol, polythiol or polyamine bearing from 3 to about 50 hydroxyl, thiol or amino groups;
each Q is a linker (and, in one or more embodiments, a hydrolytically stable linker);
each POLY$^1$ is a water-soluble, non-peptidic polymer;
each X is spacer moiety that optionally includes a releasable linkage (e.g., a hydrolyzable linkage, an enzymatically degradable linkage, and so forth);
R is a residue of a polyol, polythiol or polyamine bearing from 3 to about 50 hydroxyl, thiol or amino groups;
each Q is a linker (and, in one or more embodiments, a hydrolytically stable linker);
each POLY$^1$ is a water-soluble, non-peptidic polymer;
each X is spacer moiety that optionally includes a releasable linkage (e.g., a hydrolyzable linkage, an enzymatically degradable linkage, and so forth);
each R$^1$ is selected from the group consisting of H, a hydroxy protecting group and

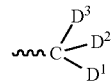

and each of D$^1$, D$^2$ and D$^3$ is independently selected from the group consisting of H, F, D and CF$_3$ (in one or more embodiments, R$^1$ is either a hydroxy protecting group or

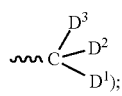

each $R^2$ is selected from the group consisting of H, a hydroxy protecting group and

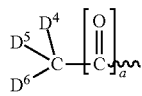

and (a) is either zero or one and each of $D^4$, $D^5$ and $D^6$ is independently selected from the group consisting of H, F, D and $CF_3$ (in one or more embodiments, $R^2$ is either a hydroxy protecting group or

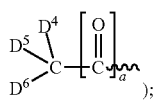

each $R^3$ is

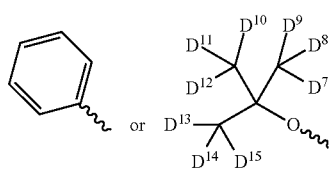

and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$; and q is a positive integer from 3 to about 50 (e.g., 4),
and pharmaceutically acceptable salts and solvates thereof.
In one or more embodiments, when the conjugates encompassed by Formula I have hydrogens at each of $R^1$ and $R^2$, $R^3$ is

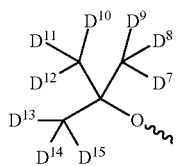

with at least one of $D^7$, $D^8$, $D^9$, $D^{10}$, $D^{11}$, $D^{12}$, $D^{13}$, $D^{14}$ and $D^{15}$ defined as F, D or $CF_3$.

As contemplated by the above structure, the conjugate has "q" number of arms, i.e., from 3 to about 50. An exemplary number of arms includes 3, 4, 5, 6, 7, 9, and 10. In one or more embodiments, the conjugates of the invention are prepared from multi-armed polymer reagents, which, in turn, are prepared from multi-arm polymers based on a multi-arm core molecule.

For example, in one approach, a multi-arm polymer can be prepared from a multi-arm core molecule by effectively "growing" a polymer onto each terminus of a multi-arm core molecule. By way of non-limiting example, it is possible to synthesize a polymer arm onto a polyol (e.g., pentaerythritol, diglycerol, etc.) via an ethoxylation reaction. In another exemplary approach, a multi-arm polymer can be prepared from a multi-arm core molecule by attaching a water-soluble, non-peptidic polymer onto each terminus of a multi-arm core molecule. The principles of both approaches are described in the literature and in, for example, U.S. Pat. No. 7,026,440. The invention, however, is not limited with regard to the specific approach taken, so long as the conjugate is encompassed by one or more of the structures provided herein.

The Residue of the Polyol, Polythiol, or Polyamine, "R"

In one or more embodiments, the residue of the polyol, polythiol or polyamine, "R," is an organic radical-containing moiety. The polyol, polythiol or polyamine from which "R" is derived possesses from about 3 to about 150 carbon atoms (e.g., from about 3 to about 50 carbon atoms, such as 3, 4, 5, 6, 7, 8, 9, and 10). The residue may contain one more heteroatoms (e.g., O, S, or N). In addition, the residue may be linear. In some instances, the residue may be cyclic.

As previously indicated, the residue of the polyol, polythiol or polyamine, "R," that forms the basis of the branching for the multi-armed conjugates provided herein, originated from a corresponding polyol, polythiol or polyamine (prior to be incorporated into the multi-arm structures containing a water-soluble, non-peptidic polymer). In one or more embodiments, the corresponding polyol, polythiol, or a polyamine bears at least three hydroxyl, thiol, or amino groups, respectively, available for polymer attachment. A "polyol" is a molecule comprising three or more hydroxyl groups. A "polythiol" is a molecule that comprises three or more thiol groups. A "polyamine" is a molecule comprising three or more amino groups.

In one or more embodiments, the polyol, polyamine or polythiol will typically contain 3 to about 25 hydroxyl, or amino groups or thiol groups, respectively, such as from 3 to about 10 (i.e., 3, 4, 5, 6, 7, 8, 9, 10) hydroxyl, amino groups or thiol groups, respectively, preferably from 3 to about 8 (i.e., 3, 4, 5, 6, 7, or 8) hydroxyl, amino groups or thiol groups, respectively. In one or more embodiments, the number of atoms between each hydroxyl, thiol, or amino group will vary, although lengths of from about 1 to about 20 (e.g., from 1 to about 5) intervening atoms, such as carbon atoms, between each hydroxyl, thiol or amino group, are exemplary. In referring to intervening core atoms and lengths, —$CH_2$— is considered as having a length of one intervening atom, —$CH_2CH_2$— is considered as having a length of two atoms, and so forth.

Exemplary polyols and polyamines (for which corresponding residues could be present in the conjugates provided herein) have a (Radical)-$(OH)_q$ and (Radical)-$(NH_2)_q$ structures, respectively, where (Radical) corresponds to an organic-containing radical and q is a positive integer from 3 to about 50. Note that in Formula I, the variable "Q," when taken together with R, typically represents a residue of the core organic radical as described herein. That is to say, when describing polyols, polythiols and polymer amines, particularly by name, these molecules are being referenced in their form prior to incorporation into a water-soluble polymer-containing structure. So, for example, a conjugate of Formula I wherein R is a residue of the polyol, pentaerythritol $[C(CH_2OH)_4]$, the residue "R" includes carbon (i.e., "C,") and, together with "Q," represents "$C(CH_2O—)_4$."

Illustrative polyols include aliphatic polyols having from 1 to 10 carbon atoms and from 3 to 10 hydroxyl groups, including for example, trihydroxyalkanes, tetrahydroxyalkanes, polyhydroxy alkyl ethers, polyhydroxyalkyl polyethers, and the like. Cycloaliphatic polyols include straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional examples of aliphatic polyols include derivatives of glucose, ribose, mannose, galactose, and related stereoisomers. Aromatic polyols may also be used, such as 1,1,1-tris(4'-hydroxyphenyl) alkanes, such as 1,1,1-tris(4-hydroxyphenyl)ethane, 2,6-bis(hydroxyalkyl)cresols, and the like. Other core polyols that may be used include polyhydroxycrown ethers, cyclodextrins, dextrins and other carbohydrates (e.g., monosaccharides, oligosaccharides, and polysaccharides, starches and amylase).

Exemplary polyols include glycerol, trimethylolpropane, pentaerythritol, dipentaerythritol, tripentaerythritol, ethoxylated forms of glycerol, trimethylolpropane, pentaerythritol, dipentaerythritol, tripentaerythritol. Also, preferred are reducing sugars such as sorbitol and glycerol oligomers, such as diglycerol, triglycerol, hexaglycerol and the like. A 21-arm polymer can be synthesized using hydroxypropyl-β-cyclodextrin, which has 21 available hydroxyl groups. Additionally, a polyglycerol having an average of 24 hydroxyl groups is also included as an exemplary polyol.

Exemplary polyamines include aliphatic polyamines such as diethylene triamine, N,N',N''-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methylamine, and N,N-dimethyl-dipropylene-triamine. Naturally occurring polyamines that can be used in the present invention include putrescine, spermidine, and spermine. Numerous suitable pentamines, tetramines, oligoamines, and pentamidine analogs suitable for use in the present invention are described in Bacchi et al. (2002) *Antimicrobial Agents and Chemotherapy*, 46(1):55-61, which is incorporated by reference herein.

Provided below are illustrative structures corresponding to residues of polyols [although each structure is depicted with the oxygen atom ("O") derived from the corresponding hydroxyl group, each "O" can be substituted with sulfur ("S") or NH to depict the corresponding residue of a polythiol or polyamine, respectively). Note that the residues shown below would be understood in terms of compounds of Formula I as corresponding to "R" and "Q." In any event, conjugates based on any of the illustrative structures set forth below are included as part of the invention.

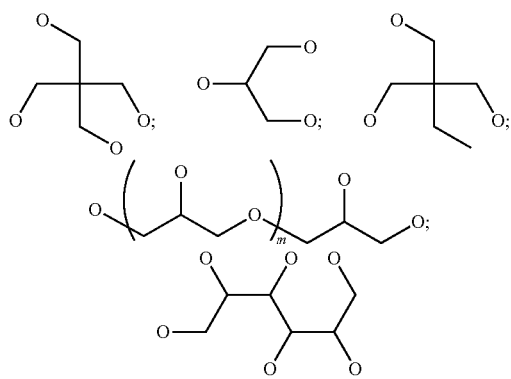

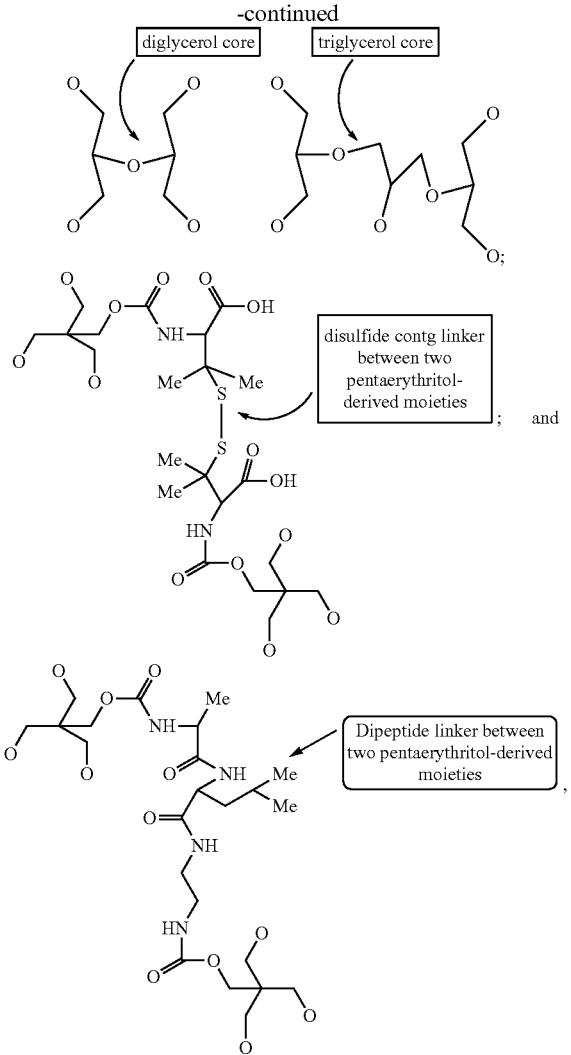

wherein m is a positive integer from 0-40 [preferably 0-10, e.g., 0-5 (i.e., 0, 1, 2, 3, 4, 5)].

Water-soluble, non-peptidic-containing multi-arm polymers (used as, for example, multi-arm polymeric reagents to prepare conjugates encompassed by Formula) based on the above-described polyols, polythiols and polyamines and others are described in WO 2007/098466, WO 2010/019233 and U.S. Pat. No. 7,744,861. These references and others describe methods for preparing such multi-arm polymers. In addition, some multi-arm polymers are available commercially from, for example, Creative PEGWorks (Winston Salem, N.C. USA), SunBio PEG-Shop (SunBio USA, Orinda, Calif.), JenKem Technology USA (Allen, Tex.), and NOF America Corporation (White Plains, N.Y.).

The Linker, "Q"

The linker, Q, serves to connect the residue of the polyol, polythiol or polyamine bearing at from 3 to about 50 hydroxyl, thiol or amino groups, "R," to each water-soluble, non-peptidic polymer, POLY$^1$, in conjugates according to Formula I. In this regard, the invention is not limited with respect to the specific linker used. In one or more embodiments, the linker between the residue, "R," and the water-soluble, non-peptidic polymer, POLY$^1$, is a hydrolytically stable linker).

In one or more embodiments of the invention, the linker, Q, is influenced by the approach used to form the multi-arm polymer employed in preparing the conjugates of the invention. For example, if a water-soluble, non-peptidic polymer bearing a functional group reactive to a hydroxyl, thiol or amine is reacted with a polyol, polythiol or polyamine, respectively, the linker, Q, may include one or more atoms incorporating the bond formed between the termini of the polyol, polythiol or polamine and the beginning of the repeating monomers of the water-soluble, non-peptidic polymer, $POLY^1$. Illustrative linking chemistries in this regard (along with the resulting linkers) are described in the literature and in, for example, Wong (1991) "*Chemistry of Protein Conjugation and Crosslinking*", CRC Press, Boca Raton, Fla., and Brinkley (1992) *Bioconjug. Chem.* 3:2013.

In one or more embodiments of conjugates of Formula I, Q contains at least one heteroatom such as O, or S, or NH, where the atom proximal to R in Q, when taken together with R, typically represents a residue of an organic radical-containing core of the polyol, polythiol or polyamine. Generally, the linker, Q, contains from 1 to about 10 atoms (e.g., from 1 to about 5 atoms). The linker, Q, typically contains a number of atoms selected from the group consisting of: 1, 2, 3, 4, 5, 6, 7, 8, 9, or 10. Illustrative Qs include O, S, —NH—, —NH—C(O)— and —C(O)—NH—.

The Water-Soluble, Non-Peptidic Polymer, $POLY^1$

The conjugates of the invention include several water-soluble, non-peptidic polymers as part of the overall structure. With respect to conjugates, each the water-soluble, non-peptidic polymer in the conjugate (e.g., $POLY^1$ in connection with compounds encompassed by Formula I) is independently selected, although preferably, each water-soluble, non-peptidic polymer is the same polymer type. That is, for example, each $POLY^1$ in the multi-armed conjugate is the same.

Any of a variety of water-soluble, non-peptidic polymers that are non-peptidic and water-soluble can be used in the multi-arm conjugates and the invention is not limited in this regard. Examples water-soluble, non-peptidic polymers include poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), such as described in U.S. Pat. No. 5,629,384, and copolymers, terpolymers, and mixtures of any one or more of the above.

When the water-soluble, non-peptidic polymer, e.g., $POLY^1$, is PEG, its structure typically comprises —$(CH_2CH_2O)_n$— (wherein the terminal ethylene is covalently attached to "Q" and the terminal oxygen is attached to "X," with respect to conjugates encompassed by Formula I), where n may range from about 5 to about 400, preferably from about 10 to about 350, or from about 20 to about 300.

Exemplary molecular weights for the water-soluble, non-peptidic polymer (e.g., $POLY^1$) include: about 200, about 250, about 300, about 400, about 500, about 600, about 700, about 800, about 900, about 1,000, about 1,500, about 2,000, about 3,000, about 4,000, about 5,000, about 6,000, about 7,000, about 7,500, about 8,000, about 9,000, about 10,000, about 12,000, about 15,000, about 17,500, about 18,000, about 19,000 and about 20,000 Daltons. In terms of the molecular weight of the multi-armed polymer, exemplary molecular weights include: about 800, about 1,000, about 1,200, about 1,600, about 2,000, about 2,400, about 2,800, about 3,200, about 3,600, about 4,000, about 5,000, about 6,000, about 8,000, about 10,000, about 12,000, about 15,000, about 16,000, about 20,000, about 24,000, about 25,000, about 28,000, about 30,000, about 32,000, about 36,000, about 40,000, about 45,000, about 48,000, about 50,000, about 60,000, about 80,000 and about 100,000 Daltons. With respect to molecular weight ranges for the multi-armed polymer, exemplary ranges include: from about 800 to about 80,000 Daltons; from about 900 to about 70,000 Daltons; From about 1,000 to about 40,000 Daltons; from 5,000 to about 30,000 Daltons; and from about 20,000 to about 80,000 Daltons.

The Spacer Moiety, X

The spacer moiety, X, serves to connect the water-soluble, non-peptidic polymer (e.g., $POLY^1$ in conjugates according to Formula I) to the taxane-based compound. Optionally, included as part of the spacer moiety is a releasable linkage (such as a hydrolyzable linkage or an enzymatically degradable linkage). In this regard, the invention is not limited with respect to the specific linker used, so long as the overall linkage includes as a part of the linkage a releasable component.

As the spacer moiety, X, the spacer moiety may be selected from the group consisting of —O—, —S—, —NH—, —C(O)—, —O—C(O)—, —C(O)—O—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —O—C(O)—NH—$CH_2$—$CH_2$—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—, —$CH_2$—$CH_2$—C(O)—, —$CH_2$—C(O)—NH—$CH_2$—$CH_2$—NH—, —$CH_2$—$CH_2$—C(O)—NH—$CH_2$—$CH_2$—NH—C(O)—, —$CH_2$—$CH_2$—C(O)—NH—$CH_2$—$CH_2$—NH—C(O)—$CH_2$—, —$CH_2$—$CH_2$—$CH_2$—C(O)—NH—$CH_2$—$CH_2$—NH—C(O)—$CH_2$—$CH_2$—, —$(CH_2)_{0-6}$C(O)—, —C(O)—$(CH_2)_{0-6}$—O—C(O)—NH—$[CH_2]_{0-6}$—$(OCH_2CH_2)_{0-2}$—, —C(O)—NH—$(CH_2)_{1-6}$—NH—C(O)—, —[NH(CHR$^6$)$_{1-6}$C(=O)]$_{1-4}$— (wherein each $R^6$ is independently selected from the group consisting of H, lower alkyl and arylalkyl), —NH(CH$_2$CH$_2$O)$_{1-10}$(CH$_2$)$_{1-6}$—, —NH(CH$_2$CH$_2$O)$_{1-10}$(CH$_2$)$_{1-5}$(CHMe)(CH$_2$)$_{0-4}$—, —NH(CH$_2$CH$_2$O)$_{1-10}$(CH$_2$)$_{1-5}$(CHMe)(CH$_2$)$_{0-4}$—, and —NH—C (O)—NH—(CH$_2$)$_{1-6}$—NH—C(O)—. For purposes of the present disclosure, however, a series of atoms is not a spacer moiety when the series of atoms is immediately adjacent to a water-soluble polymer and the series of atoms is but another monomer, such that the proposed spacer moiety would represent a mere extension of the polymer chain. X can also be L$_1$-L$_2$, wherein each of L$_1$ and L$_2$ is independently an "X" as defined herein.

In one or more embodiments of the invention, the spacer moiety, X, may include a cycloalkylene group, e.g. 1,3- or 1,4-cyclohexylene.

In one or more embodiments of the invention, the spacer moiety, X, has an atom length of from about 1 atom to about 50 atoms, or more preferably from about 1 atom to about 25 atoms, or even more preferably from about 1 atom to about 10 atoms. Typically, the spacer moiety is of an atom length selected from the group consisting of 1, 2, 3, 4, 5, 6, 7, 8, 9 and 10. When considering atom chain length, only atoms contributing to the overall distance are considered. For example, a spacer having the structure, —CH$_2$—C(O)—NH—CH$_2$CH$_2$O—CH$_2$CH$_2$O—C(O)—O— has a chain length of 11 atoms, since substituents are not considered to contribute to the length of the spacer.

In one or more embodiments of the invention, the spacer moiety, X, possesses the structure: Y—Z, where Y is a spacer fragment covalently attached to Z, a hydrolytically or enzymatically degradable linkage. In certain embodiments, Z itself may not constitute a hydrolytically or enzymatically degradable linkage, however, when taken together with Y, or at least a portion of Y, forms a linkage that is hydrolytically or enzymatically degradable. Also, Z taken together with the —C(=O)—O— to which it is attached, is potentially a hydrolytically or enzymatically degradable linkage. Preferred enzymatically degradable groups include esters, disulfides, dipeptides, tripeptides and tetrapeptides. Also preferred are certain amides such as glutamides, peptoids and peptide mimics.

In one or more embodiments of the invention, when the spacer moiety, X, is Y—Z, Y will have the structure: —(CR$_x$R$_y$)$_a$—K—(CR$_x$R$_y$)$_b$—(CH$_2$CH$_2$O)$_c$—, wherein each R$_x$ and R$_y$, in each occurrence, is independently H or an organic radical selected from the group consisting of alkyl, substituted alkyl, alkenyl, substituted alkenyl, alkynyl, substituted alkynyl, aryl, and substituted aryl, a ranges from 0 to 12 (i.e., can be 0, 1, 2, 3, 4, 5, 6, 7, 8, 9, 10, 11, or 12), b ranges from 0 to 12 (i.e., can be 0, 1, 2, 3, 4, 5, 6, 7, 8, 9, 10, 11, or 12), K is selected from —C(O)—, —C(O)NH—, —NH—C(O)—, —O—, —S—, O—C(O)—, C(O)—O—, —O—C(O)—O—, O—C(O)—NH—, —NH—C(O)—O—, and c ranges from 0 to 25, and Z is selected from C(O)—O—, O—C(O)—O—, —O—C(O)—NH—, and —NH—C(O)—O—. The particular structure of K and of Z will depend upon the values of each of a, b, and c, such that none of the following linkages result in the overall structure of the spacer moiety, X: —O—O—, NH—O—, —NH—NH—.

In one or more embodiments of the invention, when the spacer moiety, X, is Y—Z, Y will have the structure: —(CR$_x$R$_y$)$_a$—K—(CR$_x$R$_y$)$_b$—(CH$_2$CH$_2$NH)$_c$—, where the variables R$_x$, R$_y$, a, b and c have the values described in the previous paragraph.

In one or more embodiments of the invention, R$_x$ and R$_y$ (as set forth in each of the two preceding paragraphs) is, in each occurrence, independently H or lower alkyl. In one or more embodiments of the invention, R$_x$ and R$_y$ are, in each occurrence, H. In yet another embodiment, "a" ranges from 0 to 5, i.e., is selected from 0, 1, 2, 3, 4, or 5. In yet another embodiment, b ranges from 0 to 5, i.e., is selected from 0, 1, 2, 3, 4, or 5. In yet another embodiment, c ranges from 0 to 10. In yet another embodiment, K is —C(O)—NH.

In one or more embodiments, the spacer moiety, X, can also include one or more amino acid residues. In such embodiments, exemplary amino acid residues are residues from the amino acids selected from the group consisting of: alanine, valine, leucine, isoleucine, glycine, threonine, serine, cysteine, methionine, tyrosine, phenylalanine, tryptophan, aspartic acid, glutamic acid, lysine, arginine, histidine, proline, and non-naturally occurring amino acids.

The Taxane-Based Compound

The multi-arm polymer conjugates described herein include a reside of a taxane-based compound having the following structure:

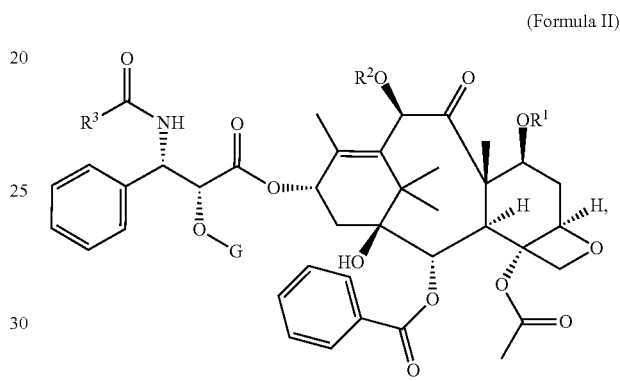

(Formula II)

wherein:

G is either H or ~C(O)—(CHR$^6$)$_{1-6}$—NH$_2$, wherein each R$^6$ is independently selected from the group consisting of H, lower alkyl and arylalkyl, and optionally, when G is ~C(O)—(CHR$^6$)$_{1-6}$—NH$_2$, the NH$_2$ group is protected;

R is a residue of a polyol, polythiol or polyamine bearing from 3 to about 50 hydroxyl, thiol or amino groups;

each Q is a linker (and, in one or more embodiments, a hydrolytically stable linker);

each POLY$^1$ is a water-soluble, non-peptidic polymer;

each X is spacer moiety that optionally includes a releasable linkage (e.g., a hydrolyzable linkage, an enzymatically degradable linkage, and so forth);

each R$^1$ is selected from the group consisting of H, a hydroxy protecting group and

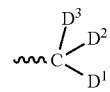

and each of D$^1$, D$^2$ and D$^3$ is independently selected from the group consisting of H, F, D and CF$_3$ (in one or more embodiments, R$^1$ is either a hydroxyl protecting group or

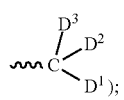);

each R$^2$ is selected from the group consisting of H, a hydroxy protecting group and

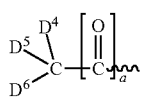

and (a) is either zero or one and each of $D^4$, $D^5$ and $D^6$ is independently selected from the group consisting of H, F, D and $CF_3$ (in one or more embodiments, $R^2$ is either a hydroxyl protecting group or

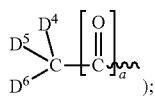
);

each $R^3$ is

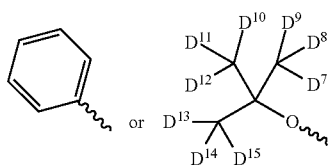

and each of $D^7$, $D^8$, $D^9$, $D^{10}$, $D^{12}$, $D^{13}$, $D^{14}$ and $D^{15}$ is independently selected from the group consisting of H, F, D and $CF_3$. In one or more embodiments, when the conjugates encompassed by the formula set forth in this paragraph have hydrogens at each of $R^1$ and $R^2$, $R^3$ is

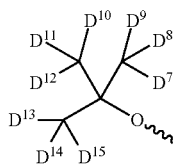

with at least one of $D^7$, $D^8$, $D^9$, $D^{10}$, $D^{12}$, $D^{13}$, $D^{14}$ and $D^{15}$ defined as F, D or $CF_3$.

Hydroxy-protected, deuterated and/or fluorinated versions the taxane-based compounds of Formula II, as well as their synthesis, are described in U.S. Provisional Patent Application Ser. No. 61/426,202 (entitled "Deuterated and/or Fluorinated Taxane Derivatives" and filed on Dec. 22, 2010) and the international application claiming priority thereto having the same title and filed on Dec. 22, 2011. In addition, taxane-based compounds of Formula II (an example of which is cabazitaxel), as well as their synthesis, are described in U.S. Pat. Nos. 5,847,170 and 5,962,705.

Method of Preparing the Conjugates of the Invention

The conjugates of the invention can be prepared using conventional synthetic approaches of organic chemistry and the invention is not limited with respect to the manner in which the conjugates are made.

In one approach for preparing conjugates of the invention, a multi-arm polymer reagent (which can be be obtained from commercially available sources, such as Creative PEG-Works, SunBio PEG-Shop, JenKem Technology USA, and NOF America Corporation, or prepared in accordance with descriptions provided in the literature) is contacted, under conjugation conditions, with an excess (typically at least a molar excess of the number of "q" polymer arms of the reagent) of the taxane-based compound. Conjugation conditions are those conditions of temperature, pH, time, solvent, and so forth that allow for covalent attachment between a reactive group of the reagent to a functional group of the taxane-based compound. Exemplary conjugation conditions between a given polymer reagent bearing a reactive group and a corresponding functional group of a taxane-based compound will be known to one of ordinary skill in the art in view of the disclosure provided herein. See, for example, Poly(ethylene glycol) Chemistry and Biological Applications, American Chemical Society, Washington, D.C. (1997).

A multi-armed polymer reagent suitable for use in connection with conjugation conditions will typically have reactive groups selected from the group consisting of: N-succinimidyl carbonate (see e.g., U.S. Pat. Nos. 5,281, 698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly (ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824, 784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900, 461). As provided in these references, exemplary conjugation conditions (including conditions of temperature, pH, time and solvent) for a given reactive group of a polymer reagent are disclosed.

In one or more embodiments, the taxane-based compound described herein may include one or more protected hydroxy groups. With respect to preparing the conjugates, in one approach, the protecting group(s) can be removed prior to conjugating the taxane-based compound with a polymer reagent. In another approach, the protecting group(s) can be removed after conjugating the taxane-based compound with a polymer reagent.

Whether before or after conjugation, hydroxy protecting groups can be removed by any suitable method and the invention is not limited in this regard. Exemplary approaches for removing hydroxy protecting groups include treatment with an acid (e.g., for acetyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, trityl, silyl ether, and ethoxyethyl ether hydroxy protecting groups), treatment with a base (e.g., for acetyl, benzoyl and pivaloyl hydroxy protecting groups), hydrogenolysis (e.g., for benzyl, methoxytrityl, p-methoxybenzyl ether and trityl hydroxy protecting groups), oxidation (e.g., for p-methoxybenzyl ether hydroxy protecting group), and treatment with BBr$_3$ is methylene chloride (e.g., for methyl ether hydroxy protecting group).

Following the initial conjugation, compositions containing the conjugates of Formula I can be purified. Methods of purification and isolation include precipitation followed by filtration and drying, as well as chromatography. Suitable chromatographic methods include gel filtration chromatography, ion exchange chromatography, and flash chromatography.

Salts of the Conjugates

The conjugates may be used in their base form. In addition, the conjugates may be used in the form corresponding to a pharmaceutically acceptable salt of the conjugate, and any reference to the conjugates of the invention herein is intended to include pharmaceutically acceptable salts. If used, a salt of a compound as described herein should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the compound with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulfonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

Compositions of Conjugates of the Invention

In certain instances, due to incomplete conversions, less than 100% yields, and other unavoidable complications routinely encountered during chemical syntheses, exemplary compositions of multi-arm conjugates are those wherein at least 80% of the multi-arm conjugates in the composition have a structure encompassed by the formula,

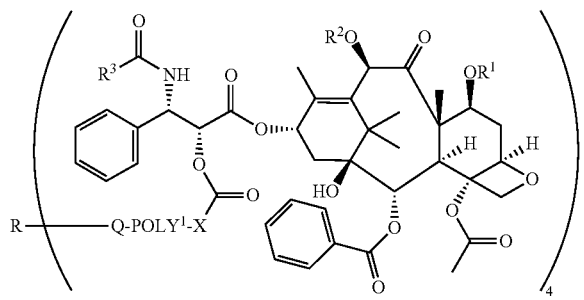

wherein:
R is a residue of polyol, polythiol or polyamine bearing from 3 to about 50 hydroxyl, thiol or amino groups;
each Q is a linker (and, in one or more embodiments, a hydrolytically stable linker);
each POLY$^1$ is a water-soluble, non-peptidic polymer;
each X is a spacer moiety that optionally includes a releasable linkage (e.g., a hydrolyzable linkage, an ezymamatically degradable linkage, and so forth);

each R$^1$ is selected from the group consisting of H, a hydroxy protecting group and

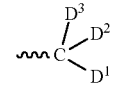

and each of D$^1$, D$^2$ and D$^3$ is independently selected from the group consisting of H, F, D and CF$_3$ (in one or more embodiments, R$^1$ is either a hydroxy protecting group or

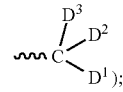

each R$^2$ is selected from the group consisting of H, a hydroxy protecting group and

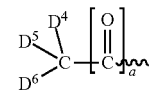

and (a) is either zero or one and each of D$^4$, D$^5$ and D$^6$ is independently selected from the group consisting of H, F, D and CF$_3$ (in one or more embodiments, R$^2$ is either a hydroxy protecting group or

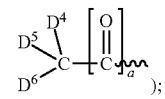

and
each R$^3$ is

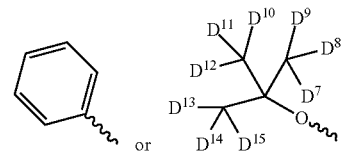

and each of D$^7$, D$^8$ D$^9$, D$^{10}$, D$^{12}$, D$^{13}$, D$^{14}$ and D$^{15}$ is independently selected from the group consisting of H, F, D and CF$_3$,
and pharmaceutically acceptable salts and solvates thereof. In one or more embodiments, when the conjugates encompassed by the formula set forth in this paragraph have hydrogens at each of R$^1$ and R$^2$, R$^3$ is

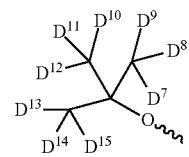

with at least one of D$^7$, D$^8$, D$^9$, D$^{10}$, D$^{11}$, D$^{12}$, D$^{13}$, D$^{14}$ and D$^{15}$ defined as F, D or CF$_3$.

Exemplary conjugates of the invention include those selected from the group consisting of:

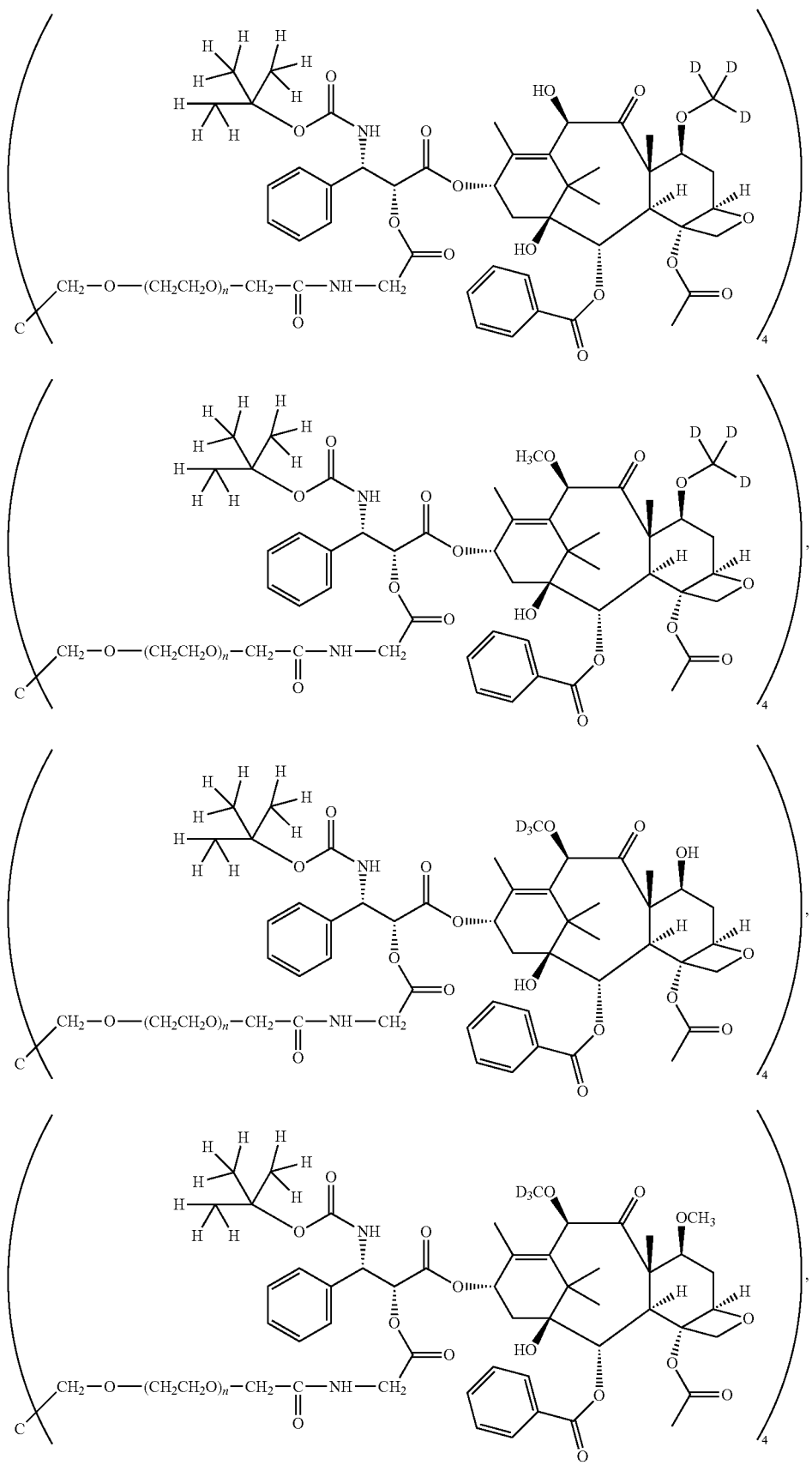

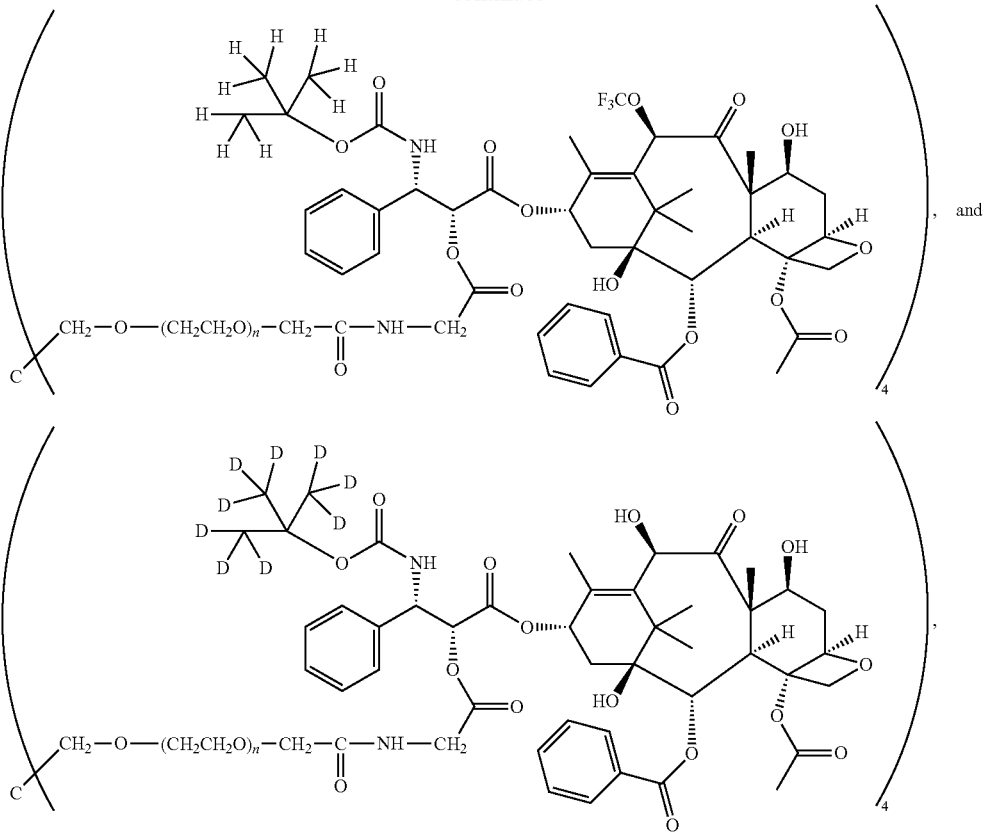

wherein each n is a positive integer from 10 to about 400.

Pharmaceutical Compositions of Conjugates of the Invention

The invention provides pharmaceutical compositions, both for veterinary and for human medical use, which comprise one or more multi-armed polymer conjugates of the invention or a pharmaceutically acceptable salt thereof, with one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80," and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy," 19$^{th}$ ed., Williams & Williams, (1995), and in the "Physician's Desk Reference," 52$^{nd}$ ed., Medical Economics, Montvale, N.J. (1998), and in "Handbook of Pharmaceutical Excipients," Third Ed., Ed. A. H. Kibbe, Pharmaceutical Press, 2000.

The conjugates may be formulated in compositions including those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. In general, the compositions are prepared by bringing the active compound into association with a liquid carrier to form a solution or a suspension, or alternatively, bringing the conjugate into association with formulation components suitable for forming a solid, optionally a particulate product, and then, if warranted, shaping the product into a desired delivery form. Solid formulations, when particulate, will typically comprise particles with sizes ranging from about 1 nanometer to about 500 microns. In general, for solid formulations intended for intravenous administration, particles will typically range from about 1 nm to about 10 microns in diameter. Particularly preferred are sterile, lyophilized compositions that are reconstituted in an aqueous vehicle prior to injection.

The amount of multi-armed polymer conjugate in the formulation will vary depending upon the specific active agent employed, its activity, the molecular weight of the conjugate, and other factors such as dosage form, target patient population, and other considerations, and will generally be readily determined by one skilled in the art. In practice, this will depending upon the particular conjugate, its activity, the severity of the condition to be treated, the patient, the stability of the formulation, and the like. Compositions will generally contain anywhere from about 1% by weight to about 99% by weight conjugate, typically from about 2% to about 95% by weight conjugate, and more typically from about 5% to 85% by weight conjugate, and will also depend upon the relative amounts of excipients/additives contained in the composition. More specifically, the composition will typically contain at least about one of the following percentages of conjugate: 2%, 5%, 10%, 20%, 30%, 40%, 50%, 60%, or more by weight.

Compositions of the present invention suitable for oral administration may be provided as discrete units such as capsules, cachets, tablets, lozenges, and the like, each containing a predetermined amount of the conjugate as a powder or granules; or a suspension in an aqueous liquor or non-aqueous liquid such as a syrup, an elixir, an emulsion, a draught, and the like.

Formulations suitable for parenteral administration conveniently comprise a sterile aqueous preparation of the prodrug conjugate, which can be formulated to be isotonic with the blood of the recipient.

Nasal spray formulations comprise purified aqueous solutions of the multi-armed polymer conjugate with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the multi-armed polymer conjugate dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol, e.g., by inhalation. These formulations comprise a solution or suspension of the desired multi-armed polymer conjugate or a salt thereof. The desired formulation may be placed in a small chamber and nebulized. Nebulization may be accomplished by compressed air or by ultrasonic energy to form a plurality of liquid droplets or solid particles comprising the conjugates or salts thereof.

Methods of Use

The multi-armed polymer conjugates provided herein can be used to treat or prevent any condition (e.g., cancer) responsive to administration of the conjugate described herein.

The multi-arm polymer conjugates of the invention are particularly useful as anticancer agents, i.e., an agent that can reduce the growth of one or more tumors. Exemplary cancer types include, but are not limited to, breast cancer, ovarian cancer, colon cancer, colorectal cancer, prostate cancer, gastric cancer, malignant melanoma, small cell lung cancer, non-small cell lung cancer, thyroid cancers, kidney cancer, cancer of the bile duct, brain cancer, cancer of the head and neck, lymphomas, leukemias, rhabdomyosarcoma, and neuroblastoma.

Methods of administration comprise administering to a mammal in need thereof a therapeutically effective amount of a composition or formulation containing a multi-arm polymer conjugate as provided herein. A therapeutically effective dosage amount of any specific multi-arm polymer conjugate will vary from conjugate to conjugate, patient to patient, and will depend upon factors such as the condition of the patient, the activity of the particular active agent employed, the route of delivery, and condition being treated.

Methods of treatment also include administering a therapeutically effective amount of a composition or formulation comprising a multi-arm polymer conjugate as described herein with a second anticancer agent (such as, for example, 5-fluorouracil, leucovorin, avastin, cetuximab, panitumumab, xeloda, abraxane, cis-platin, carboplatin, gemcitabine, and pemetrexed.

The multi-arm polymer conjugate of the invention may be administered once or several times a day, preferably once a day or less. Illustrative dosing schedules include once per week, once every two weeks, or once every three weeks. In the instance of a maintenance dose, dosing may take place even less frequently than once every three weeks, such as once monthly. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

The practice of the invention will employ, unless otherwise indicated, conventional techniques of organic synthesis and the like, which are within the skill of the art. Such techniques are fully described in the literature. Reagents and materials are commercially available unless specifically stated to the contrary. See, for example, M. B. Smith and J. March, *March's Advanced Organic Chemistry: Reactions Mechanisms and Structure*, 6th Ed. (New York: Wiley-Interscience, 2007), supra, and Comprehensive Organic Functional Group Transformations II, Volumes 1-7, Second Ed.: A Comprehensive Review of the Synthetic Literature 1995-2003 (Organic Chemistry Series), Eds. Katritsky, A. R., et al., Elsevier Science.

Example 1

Synthesis of 4-ARM-PEG$_{20K}$-Butanoic Acid ("4-ARM-PEG$_{20K}$-BA")

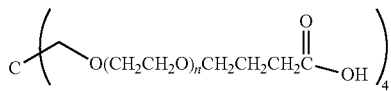

A solution of pentaerythritol-based 4-ARM-PEG$_{20K}$-OH (100.0 g, 0.020 equivalents) (NOF Corporation) in toluene (750 ml) was azeotropically dried by distilling off 150 ml of toluene. A 1.0M solution of potassium tert-butoxide in tert-butanol (60 ml, 0.060 moles) and 1-(3-bromopropyl)-4-methyl-2,6,7-trioxabicyclo[2,2,2]octane (12.6 g, 0.052 moles) was added and the mixture was stirred overnight at 70° C. under argon atmosphere. The solvent was distilled off under reduced pressure and the residue was dissolved in distilled water (1,000 ml). The pH of the solution was adjusted to 2 with 5% phosphoric acid and the solution was stirred for 15 minutes at room temperature. Next, the pH was readjusted to 12 by addition of 1M sodium hydroxide, and the solution was stirred for two hours keeping the pH at 12 by periodic addition of 1M sodium hydroxide. Thereafter, the pH was adjusted to 3 by addition of 5% phosphoric acid and the product was extracted with dichloromethane.

The extract was dried over anhydrous magnesium sulfate, filtered, and then added to isopropyl alcohol. The precipitated product was removed by filtration and dried under reduced pressure.

Yield 95.0 g. $^1$H NMR (d$_6$-DMSO): δ 1.72 ppm (q, C$\underline{H_2}$—CH$_2$—COO—), 2.24 Ppm (t, —CH$_2$—COO—), 3.51 ppm (s, PEG backbone). Substitution=~100% (meaning that, within the sensitivity of the method, the OH— groups located on the end of each arm of the 4-ARM-PEG starting material were converted to the corresponding butanoic acid).

Example 2

Synthesis of 4-ARM-PEG$_{20K}$-Acetic Acid ("4-ARM-PEG$_{20K}$-CM")

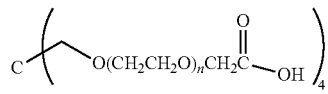

A solution of pentaerythritol-based 4-ARM-PEG$_{20K}$-OH (100.0 g, 0.020 equivalents) (NOF Corporation) in toluene (750 ml) was azeotropically dried by distilling off 150 ml of toluene. 1.0M solution of potassium tert-butoxide in tert-butanol (60 ml, 0.060 moles) and tert-butyl bromoacetate (12.9 g, 0.066 moles) were added and the mixture was stirred overnight at 45° C. under argon atmosphere. The solvent was distilled off under reduced pressure and the residue was dissolved in distilled water (1,000 ml). The pH of the solution was adjusted to 12 by addition of 1M sodium hydroxide and the solution was stirred overnight keeping the pH at 12.0 by periodic addition of 1M sodium hydroxide. The pH was adjusted to 2 by addition of 1M phosphoric acid. The resulting product, 4-ARM-PEG$_{20K}$-acetic acid (also referred to as "4-ARM-PEG$_{20K}$-CM") was extracted with dichloromethane. The extract was dried over anhydrous sodium sulfate, filtered, and concentrated. The concentrated extract was then added to ethyl ether.

The precipitated product was collected by filtration and dried under reduced pressure. Yield 95.5 g. $^1$H NMR (d$_6$-DMSO): δ 3.51 ppm (s, PEG backbone), 4.01 ppm (s, —CH$_2$—COO—). Substitution ~100% (meaning that, within the sensitivity of the method, the OH— groups located on the ends of each arm of the 4-ARM-PEG starting material was converted to the corresponding acetic acid).

Example 3

Synthesis of 4-ARM-PEG$_{20K}$-Acetic Acid, N-Hydroxysuccinimide ester ("4-ARM-PEG$_{20K}$-SCM")

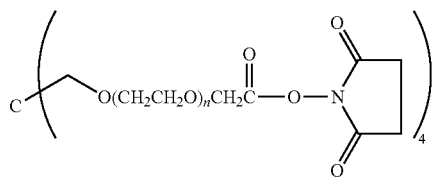

4-ARM-PEG$_{20K}$-acetic acid (90.0 g, 0.018 equivalents) was dissolved in dichloromethane (270 ml) and N-hydroxysuccinimide (2.20 g, 0.019 mol) was added. Next, dicyclohexylcarbodiimide (4.13 g, 0.020 moles) was added, and the solution was stirred at room temperature overnight. The reaction mixture was filtered, concentrated, and precipitated by addition to isopropyl alcohol.

Yield of final product: 82 g. $^1$H NMR (d$_6$-DMSO): δ 2.81 ppm (s, succinimide), 3.51 ppm (s, PEG backbone), 4.60 ppm (s, —CH$_2$—COO—). Substitution ~100%.

Example 4

Preparation of d$_6$-Cabazitaxel (7β,10β-(d$_6$)-Dimetdocetaxel)

Synthesis of 7β,10β-(d$_6$)-Dimethoxy-10-Deacetylbaccatin III

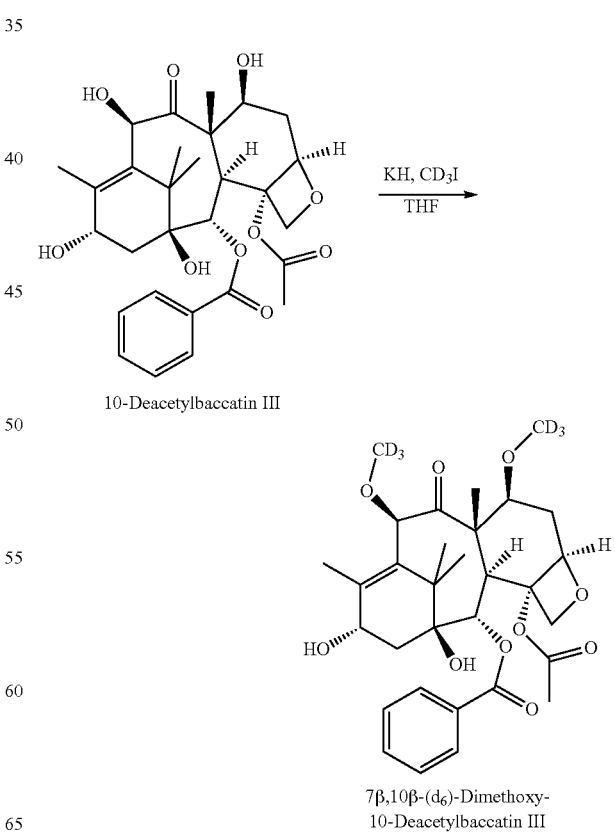

10-Deacetylbaccatin III

7β,10β-(d$_6$)-Dimethoxy-10-Deacetylbaccatin III

A suspension of 10-deacetylbaccatin III (Sigma-Aldrich; 2.2 g) in tetrahydrofuran (25 ml) and a solution of methyl-($d_3$) iodide (9.5 g) in tetrahydrofuran (10 ml) was simultaneously added dropwise to a suspension of potassium hydride (5.0 g), in tetrahydrofuran (15 ml) at −20° C. Next, the reaction mixture was stirred for eight hours at room temperature. Then, the reaction mixture was added to water (100 ml) and the resulting mixture was stored overnight at 4° C. Diisopropyl ether (100 ml) was added and the solid precipitate was filtered off. The crude product was purified by silica gel chromatography giving 0.75 g of the desired 7β,10β-($d_6$)-dimethoxy-10-deacetylbaccatin III having 98% purity as determined by HPLC analysis.

Synthesis of $d_6$-Cabazitaxel

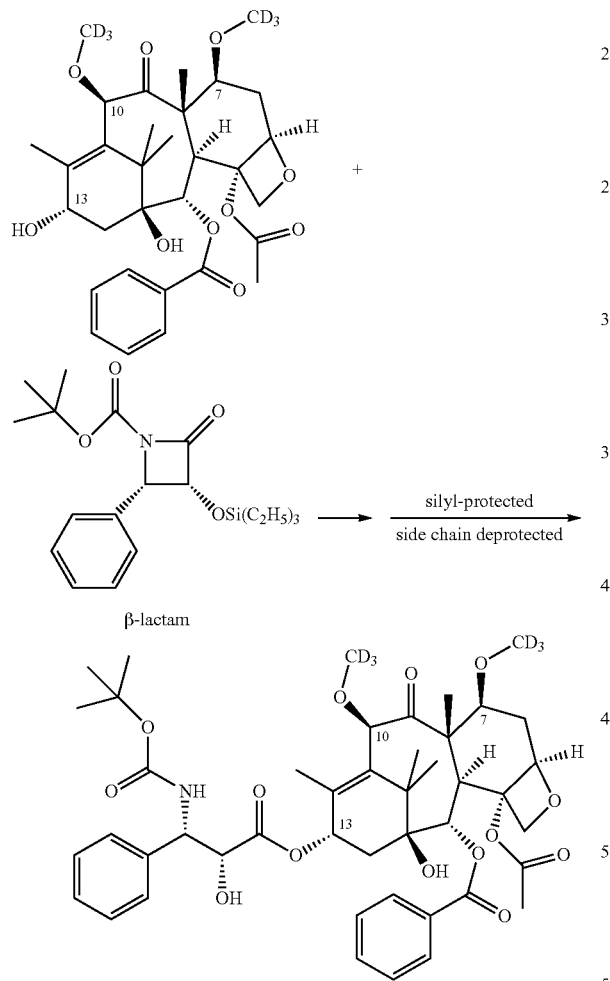

β-lactam

Dicyclohexylcarbodiimide (0.40 g) and then 4-(N,N-dimethylamino)pyridine (0.06 g) were added to a suspension of 7β,10β-($d_6$)-dimethoxy-10-deacetylbaccatin III (0.65 g), β-lactam shown above (0.60 g), and powdered 4 A molecular sieves (0.15 g) in 6 ml of ethyl acetate. The mixture was stirred overnight at room temperature under an argon atmosphere, and was concentrated to dryness under reduced pressure. The resulting residue was purified by silica gel chromatography giving the corresponding 2'-triethylsilyl-7β,10β-($d_6$)-dimethoxydocetaxel in the form of a white solid (0.55 g).

The product was dissolved in 0.2N solution of hydrogen chloride in ethyl alcohol (40 ml) and stirred overnight at 0° C. under a nitrogen atmosphere. Next, the reaction mixture was diluted with distilled water (15 ml) and the product was extracted two times with dichloromethane (2×60 ml). The extract was dried (MgSO$_4$) and concentrated to dryness under reduced pressure. The crude product was purified by silica gel chromatography giving 0.45 g of the desired $d_6$-cabazitaxel.

Example 5

Preparation of 10β-($d_3$)-Methoxydocetaxel

Synthesis of 7β-Triethylsilyl-10-Deacetylbaccatin III

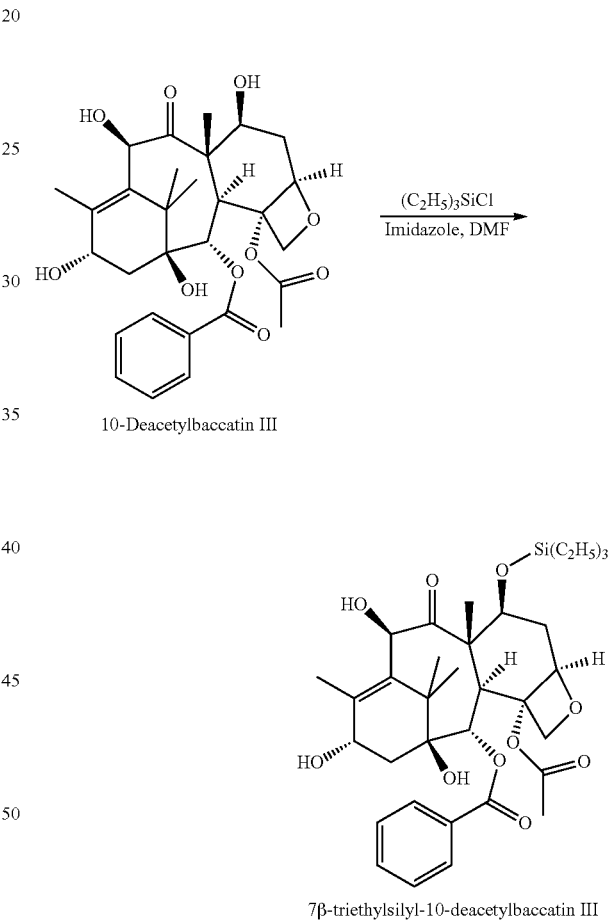

10-Deacetylbaccatin III

7β-triethylsilyl-10-deacetylbaccatin III

Chlorotriethylsilane (3.7 ml, 0.0221 mol) was added dropwise at 0° C. to a solution of 10-deacetylbaccatin III (3.00 g, 0.0056 mol) and imidazole (1.50 g, 0.0222 mmol) in 140 ml of N,N-dimethylformamide (DMF) and the reaction mixture was stirred for two hours at 0° C. Next, ethyl acetate was added and the obtained solution was washed with water, brine, dried with MgSO$_4$ and concentrated to dryness. The crude product was purified by silica gel chromatography using hexane:EtOAc=1:1 as an eluent to give 3.35 g of 7β-triethylsilyl-10-deacetylbaccatin III as a white solid.

Synthesis of 7β-Triethylsilyl,10β-(d₃)-Methoxy-10-Deacetylbaccatin III

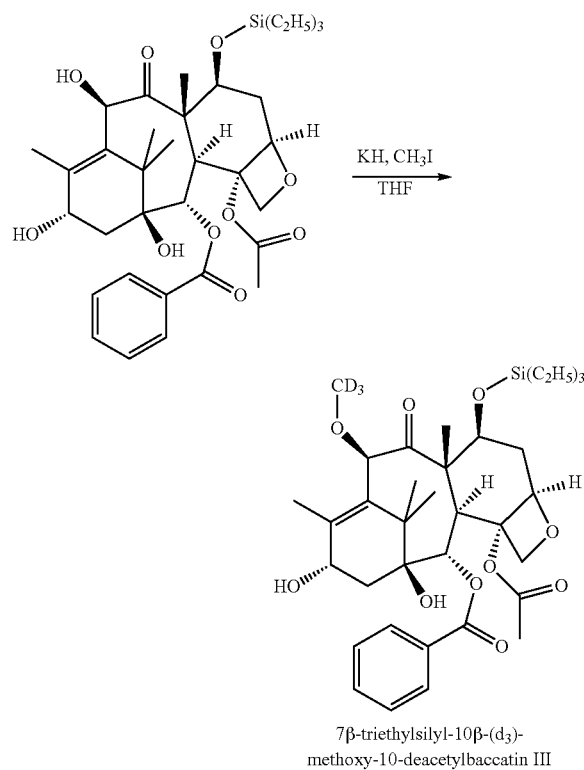

7β-triethylsilyl-10β-(d₃)-methoxy-10-deacetylbaccatin III

A suspension of 7β-triethylsilyl-10-deacetylbaccatin III (2.7 g) in tetrahydrofuran (25 ml) and a solution of methyl-(d₃) iodide (9.5 g) in tetrahydrofuran (10 ml) was simultaneously added dropwise to a suspension of potassium hydride (5.0 g) in tetrahydrofuran (15 ml) at −20° C. Next, the reaction mixture was stirred for eight hours at room temperature. Then, the reaction mixture was added to water (100 ml) and the resulting mixture was stored overnight at 4° C. Diisopropyl ether (100 ml) was added and the solid precipitate was filtered off. The crude product was purified by silica gel chromatography giving 0.85 g of the desired 7β-triethylsilyl-10β-(d₃)-methoxy-10-deacetylbaccatin III having 97% purity as determined by HPLC analysis.

Synthesis of 10β-(d₃)-Methoxydocetaxel

Dicyclohexylcarbodiimide (0.40 g) and then 4-(N,N-dimethylamino)pyridine (0.06 g) were added to a suspension of 7β-triethylsilyl,10β-(d₃)-methoxy-10-deacetylbaccatin III (0.80 g), β-lactam showed above (0.60 g), and powdered 4 A molecular sieves (0.15 g) in 6 ml of ethyl acetate. The mixture was stirred overnight at room temperature under an argon atmosphere, and was concentrated to dryness under reduced pressure. The resulting residue was purified by silica gel chromatography giving 2'-triethylsilyl-7β-triethylsilyl-10β-(d₃)-methoxydocetaxel in the form of a white solid (0.70 g).

The product was dissolved in 0.2N solution of hydrogen chloride in ethyl alcohol (40 ml) and stirred overnight at 0° C. under the nitrogen atmosphere. Next, the reaction mixture was diluted with distilled water (15 ml) and the product was extracted two times with dichloromethane (2×60 ml). The extract was dried (MgSO₄) and concentrated to dryness under reduced pressure. The crude product was purified by silica gel chromatography giving 0.52 g of the desired 10β-(d₃)-methoxydocetaxel.

Example 6

Preparation of 3'-(1,1,1-Trifluoromethyl-2-Propoxycarbonyloxyimino)-Docetaxel

Synthesis of 3'-Aminodocetaxel

-continued

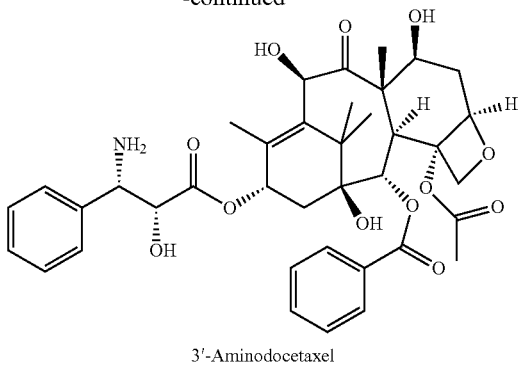

3'-Aminodocetaxel

Docetaxel (0.600 g, 0.00074 mol) was dissolved in 50 ml of concentrated formic acid, and the solution was stirred for four hours at room temperature. Next, formic acid was distilled off under reduced pressure. The residue was dissolved in toluene and then toluene was distilled off. This operation was repeated several times to remove residual formic acid. The solid residue was washed with 5% NaHCO₃ solution (2×100 ml), and then the product was extracted with ethyl acetate. The extract was dried (MgSO₄) and the solvent was distilled off under reduced pressure.

The crude product was purified by silica gel chromatography using a mixture EtOAc/MeOH=95/5 mixture as an eluent giving 0.45 g of pure 98.5% pure 3'-aminodocetaxel.

Synthesis of 3'-(1,1,1-trifluoromethyl-2-propoxycarbonyloxyimino)-docetaxel

3'-Aminodocetaxel (0.300 g) and 2-(1,1,1-trifluoromethyl-2-propoxycarbonyloxyimino)-2-phenylacetonitrile (0.100 g) were dissolved in pyridine (10 ml). The reaction mixture was stirred overnight at room temperature under nitrogen atmosphere. Next, the solvent was distilled off and the crude compound was purified by silica gel chromatography giving 0.205 g of the desired 3'-(1,1,1-trifluoromethyl-2-propoxycarbonyloxyimino)-docetaxel having purity >98% as determined by RP HPLC.

Example 7

Preparation of d₉-Docetaxel

Synthesis of 3'-Aminodocetaxel

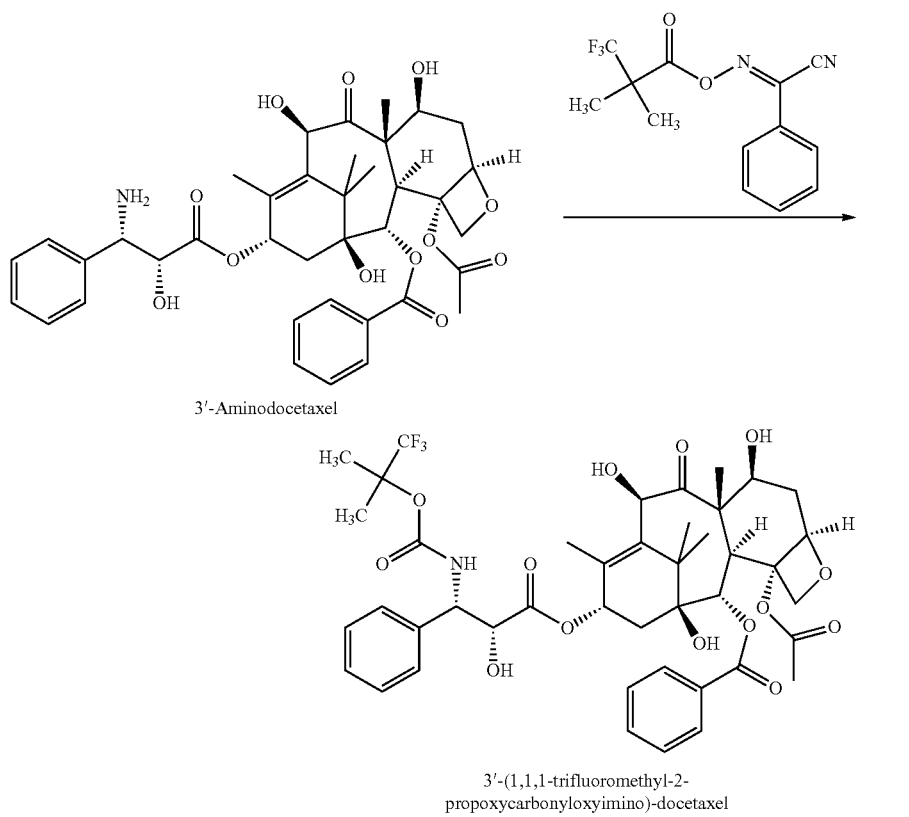

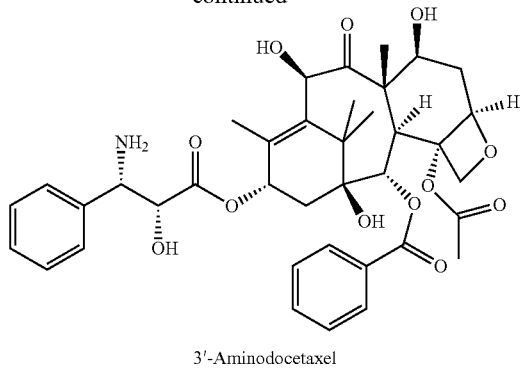

3'-Aminodocetaxel

Docetaxel (10.0 g) was dissolved in 300 ml of concentrated formic acid at ~5° C. and the solution was stirred at ~5° C. The reaction progress was monitored by reversed phase HPLC. After 4 to 6 hours of the reaction, the solvent was evaporated to dryness under reduced pressure (t max 40° C.). The wet product was dried under vacuum overnight.

Synthesis of $d_9$-tert-Butyl Benzotriazolyl Carbonate

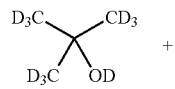

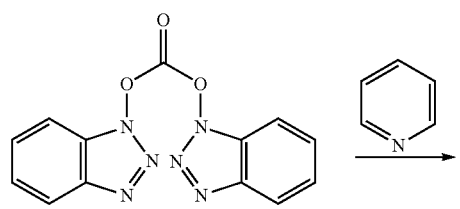

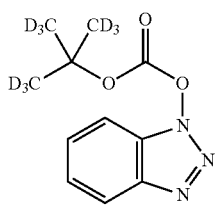

d-10-tert-Butanol (Aldrich; MW=84.08; 13.67 g, 0.1624 mol) was dissolved in 140 ml of anhydrous acetonitrile, followed by the addition of dibenzotriazolyl carbonate (DiBTC; MW=296.2; 66.7% dispersion in 1,1,2-trichloroethane; 68.5 g, 0.1542 mol) with 680 ml of anhydrous acetonitrile. The reaction mixture was stirred 15 minutes, then pyridine (37.8 ml) was added. The reaction mixture was stirred overnight at room temperature under a nitrogen atmosphere. The precipitated side products were filtered off. The obtained solution (858 ml) was used directly in the next step of the synthesis. (Calculated concentration of the $d_9$-tert-Butyl Benzotriazolyl Carbonate solution was ~0.180 mmol/ml.)

Synthesis of $d_9$-Docetaxel

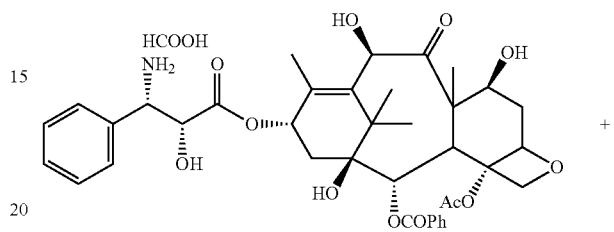

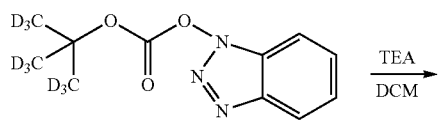

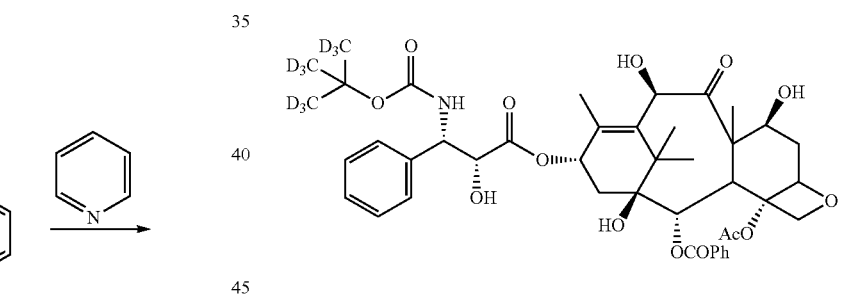

3'-Aminodocetaxel (0.01238 mol) was dispersed in 200 ml of anhydrous acetonitrile, next a solution of $d_9$-tert-butyl benzotriazolyl carbonate (207 ml; 0.0373 mol) was added, followed by the addition of anhydrous triethylamine (TEA) (8.6 ml, 0.0617 mol; 5.0 fold excess). The reaction mixture was stirred at room temperature for five hours. The solvent was evaporated to dryness at 35-40° C. under reduced pressure. The residue was dissolved in 500 ml of dichloromethane and the solution was washed with 0.1M aq. $NaH_2PO_4$ (100 ml×2). After drying with $MgSO_4$, the solution was filtered and the filtrate was concentrated to dryness at 35-40° C. under reduced pressure. The wet product was dried under vacuum for overnight. Next, the product was purified by silica gel chromatography using dichloromethane-ethyl acetate mixture as an eluent. Yield: 4.7 g; HPLC purity ~97% (UV 254 nm detector) 100% (ELSD detector).

Example 8

Synthesis of 4-ARM-PEG$_{20K}$-Butanoate-Linked d$_6$-Cabazitaxel Conjugate ("4-ARM-PEG$_{20K}$-BA-d$_6$-CAB")

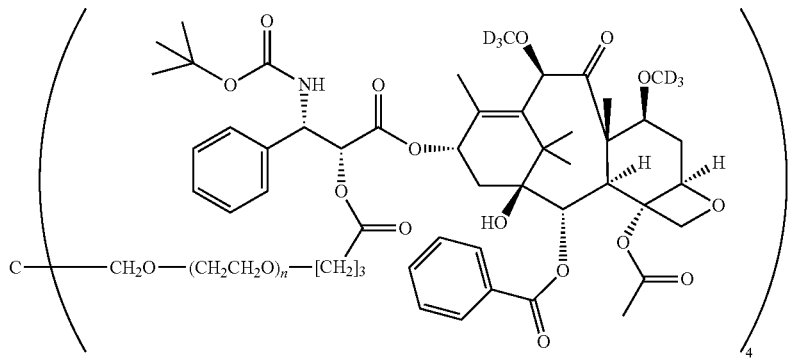

To a solution of 4-ARM-PEG$_{20K}$-butanoic acid (5.0 g, 0.0010 equivalents, Example 1), d$_6$-cabazitaxel (1.0 g, 0.0012 moles), and p-toluenosulfonic acid 4-dimethylaminopyridine salt (1.5 g, 0.0051 moles) in 60 ml of anhydrous dichloromethane was added N,N'-diisopropylcarbodiimide (0.63 g, 0.005 mole) and the mixture was stirred overnight at room temperature under an argon atmosphere. The solvent was distilled off under reduced pressure. The residue was dissolved in dichloromethane (7.5 ml) and added to a 1:1 mixture of isopropyl alcohol and diethyl ether (100 ml). The precipitated product was filtered off and dried under reduced pressure. The precipitation was repeated giving 4.0 g of white solid product.

NMR analysis of the product in CDCl$_3$ as a solvent showed that to each molecule of 4ARM-PEG$_{20K}$-butanoic acid (4-ARM-PEG$_{20K}$-BA) was connected ~4 molecules of d$_6$-cabazitaxel. $^1$H NMR (CDCl$_3$): δ 8.10 (d, 8H), 7.58 (m, 4H), 7.44 (m, 8H), 7.30 (m, 8H), 7.24 (m, 8H), 6.25 (t, 4H), 5.62 (d, 4H), 5.48 (m, 8H), 5.28 (s, 4H), 5.00 (d, 4H), 4.82 (s, 4H), 4.30 (d, 4H), 4.15 (d, 4H), 3.90 (m, 4H), 3.85 (d, 4H), 3.80-3.40 (m, 1891H), 3.41 (s, 3H), 3.30 (s, 3H), 2.70 (m, 4H), 2.52 (m, 4H), 2.43 (m, 14H), 2.30 (m, 4H), 2.15 (m, 4H), 2.00 (s, 12H), 1.85 (m, 8H), 1.80 (m, 4H), 1.70 (s, 12H), 1.35 (s, 36H), 1.19 (m, 24H).

Example 9

Synthesis of 4-ARM-PEG$_{20K}$-Acetate-Linked 10β-(d$_3$)-Methoxydocetaxel Conjugate ("4-ARM-PEG$_{20K}$-CM-10-d$_3$-MDOC")

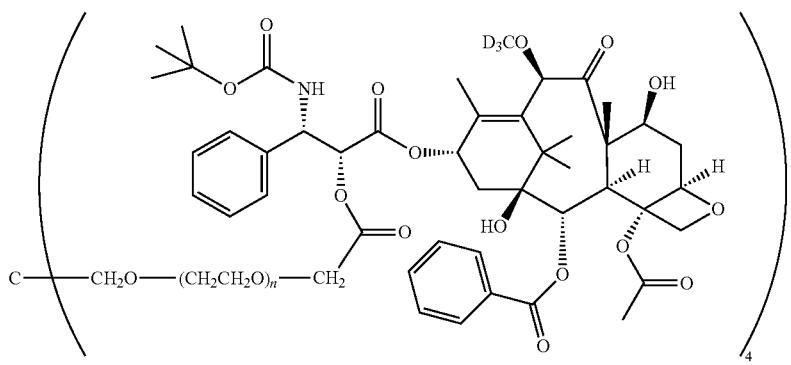

To a solution of 4-ARM-PEG$_{20K}$-acetic acid (5.0 g, 0.0010 equivalents, Example 2), 10β-(d$_3$)-methoxydocetaxel (1.0 g, 0.0012 moles), and p-toluenosulfonic acid 4-dimethylaminopyridine salt (1.5 g, 0.0051 moles) in 60 ml of anhydrous dichloromethane, was added N,N'-diisopropylcarbodiimide (0.63 g, 0.005 mole) and the mixture was stirred overnight at room temperature under an argon atmosphere. The solvent was distilled off under reduced pressure. The residue was dissolved in dichloromethane (7.5 ml) and added to a 1:1 mixture of isopropyl alcohol and diethyl ether (100 ml). The precipitated product was filtered off and dried under reduced pressure. The precipitation was repeated giving 3.9 g of white solid product.

NMR analysis of the product in CDCl$_3$ as a solvent showed that to each molecule of 4ARM-PEG$_{20K}$-acetic acid (4-ARM-PEG$_{20K}$-CM) was connected ~4 molecules of 10β-(d$_3$)-methoxydocetaxel.

Example 10

Synthesis of 4-ARM-PEG$_{20K}$-Acetate-Linked 3'-(1,1,1-Trifluoromethyl-2-propoxycarbonyloxyimino)-Docetaxel Conjugate ("4-ARM-PEGCM-10-TF3-DOC")

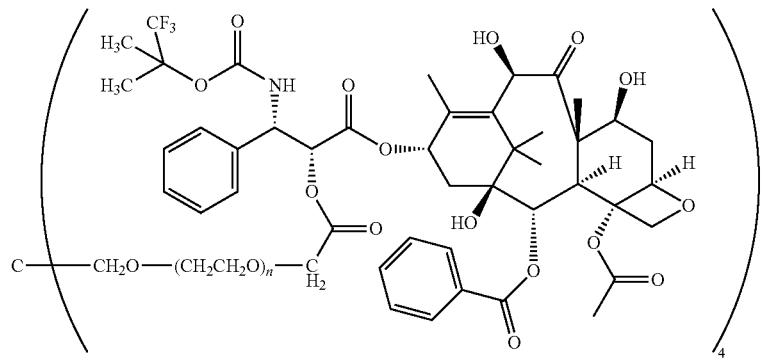

Example 9 was repeated using instead of 10β-(D$_3$)-methoxydocetaxel the same molar amount of 3'-(1,1,1-trifluoromethyl-2-propoxycarbonyloxyimino)-docetaxel.

NMR analysis of the obtained product showed that to each molecule of 4ARM-PEG$_{20K}$-acetic acid (4-ARM-PEG$_{20K}$-CM) was connected ~4 molecules of 3'-(1,1,1-trifluoromethyl-2-propoxycarbonyloxyimino)-docetaxel.

Example 11

Synthesis of d$_6$-Cabazitaxel-2'-O-Alaninate (7β, 10β-(d$_6$)-Dimethoxydocetaxel-2'-O-Alaninate)

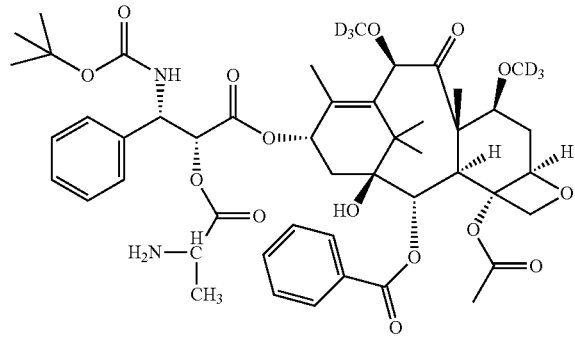

N-CBZ-(D,L)-Alanine (0.52 g, 0.00233 mol) was dissolved in 200 mL of anhydrous dichloromethane at room temperature. To this solution, N,N'-diisopropylcarbodiimide (DIPC; 0.75 ml 0.00469 mol), 4-dimethylaminopyridine (DMAP; 0.38 g, 0.00313 mol), and d$_6$-cabazitaxel (1.31 g, 0.00157 mol) were added at 0° C. Then the reaction mixture was stirred overnight at room temperature under nitrogen atmosphere. The solution was washed with 0.1N HCl, dried and concentrated to dryness under reduced pressure. The crude product (1.72 g) was purified by silica gel chromatography to give 1.4 g of d$_6$-cabazitaxel-2'-ester of N-CBZ-(D,L)-alanine.

$^1$H NMR (CDCl$_3$): δ 8.13 (d, 2H), 7.63 (m, 1H), 7.51 (m, 2H), 7.35 (m, 10H), 6.27 (t, 1H), 5.65 (d., 1H), 5.52 (br., 1H), 5.42 (m, 1H), 5.35 (s, 1H), 5.25 (d, 1H), 5.10 (m, 2H), 5.00 (d, 1H), 4.82 (s, 1H), 4.50 (m, 1H), 4.32 (d, 1H), 4.20 (d, 1H), 3.90 (m, 2H), 3.45 (s, 3H), 3.30 (s, 3H), 2.72 (m, 1H), 2.46 (s, 3H), 2.32 (m, 1H), 2.22 (m, 1H), 2.00 (s, 3H), 1.80 (t, 1H), 1.72 (s, 3H), 1.36 (s, 9H), 1.24 (m, 9H).

Removal of CBZ protective group was achieved by hydrogenation (hydrogen pressure 40 psi, 5 hours) performed in tetrahydrofuran (THF; 20 ml), in the presence of hydrogenation catalyst (10% of palladium hydroxide on the active carbon; 0.14 g). The crude product was purified by silica gel chromatography giving the desired d$_6$-cabazitaxel-2'-O-alaninate (0.88 g).

$^1$H NMR (CDCl$_3$): δ 8.13 (d, 2H), 7.63 (m, 1H), 7.51 (m, 2H), 7.40 (m, 2H), 7.30 (m, 3H), 6.27 (t, 1H), 5.52 (br., 1H), 5.45 (m, 2H), 5.00 (d, 1H), 4.85 (s, 1H), 4.32 (d, 1H), 4.20 (d, 1H), 3.90 (m, 1H), 3.85 (m, 1H), 3.65 (m, 1H), 2.72 (m, 1H), 2.46 (s, 3H), 2.32 (m, 1H), 2.22 (m, 1H), 2.00 (s, 3H), 1.80 (t, 1H), 1.72 (s, 3H), 1.36 (s, 9H), 1.22 (d, 6H), 1.15 (d, 3H).

Example 12

Synthesis of 4-ARM-PEG$_{20K}$-Alaninate-Linked d$_6$-Cabazitaxel Conjugate ("4-ARM-PEG$_{20K}$-CM-ALA-d$_6$-CAB")

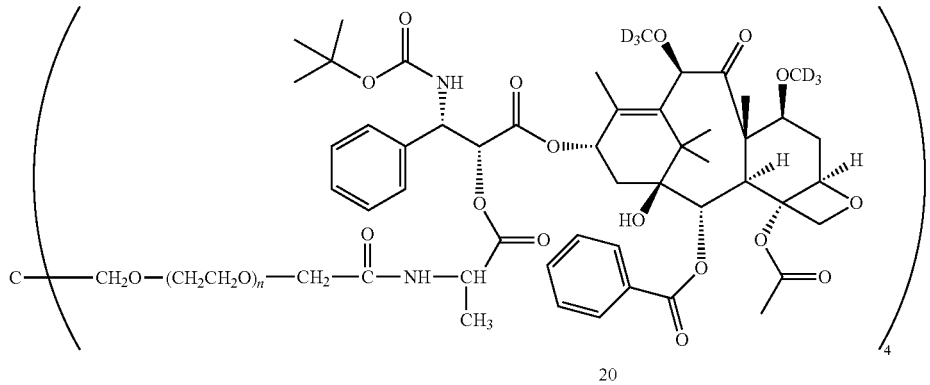

4-ARM-PEG$_{20K}$-acetic acid, N-hydroxysuccinimide ester (3.70 g, 0.000740 equivalents; Example 3) was added slowly to the solution of d$_6$-cabazitaxel-2'-O-alaninate (0.80 g, 0.000882 moles) in dichloromethane (40 ml) containing triethylamine (0.35 g). The solution was stirred at room temperature overnight. The reaction mixture was concentrated to dryness by distilling off dichloromethane under reduced pressure. The crude product was dissolved in 120 ml dichloromethane and precipitated by addition of isopropyl alcohol.

The precipitate, (4-ARM-PEG$_{20K}$-CM-ALA-d$_6$-CAB) was collected and dried to provide 3.4 g of a white solid product. NMR analysis of the product in CDCl$_3$ as a solvent showed that to each molecule of 4ARM-PEG$_{20K}$-alaninate (4-ARM-PEG$_{20K}$-CM-ALA) was connected ~4 molecules of d$_6$-cabazitaxel.

$^1$H NMR (CDCl$_3$): δ 8.12 (d, 8H), 7.60 (m, 4H), 7.50 (m, 8H), 7.40 (m, 12H), 7.30 (m, 8H), 6.25 (t, 4H), 5.65 (m, 8H), 5.50 (br., 4H), 5.38 (s, 4H), 5.00 (d, 4H), 4.82 (s, 4H), 4.70 (m, 4H), 4.30 (d, 4H), 4.15 (d, 4H), 4.00 (d, 4H), 3.90 (m, 4H), 3.85 (m, 8H), 3.80 (m, 8H), 3.76-3.46 (m, 1926H), 2.72 (m, 4H), 2.42 (s, 12H), 2.32 (m, 4H), 2.22 (m, 4H), 2.00 (s, 12H), 1.80 (t, 4H), 1.70 (s, 12H), 1.35 (m, 48H), 1.20 (d, 24H).

Example 13

Synthesis of D$_9$-Docetaxel-2'-O-Alaninate

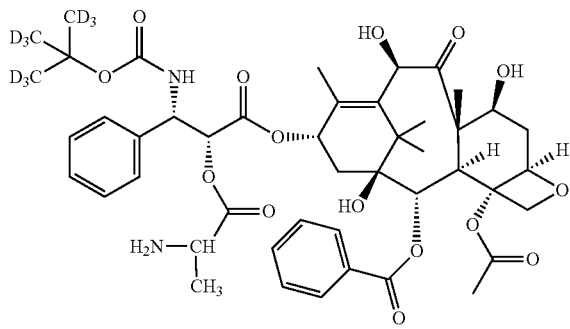

d$_9$-Docetaxel (2.0 g; 0.00245 mol), 1:1 salt of 4-(dimethylamino)pyridine and p-toluensulfonic acid (DPTS), 0.38 g, 0.0012 mol), and N,N'-diisopropylcarbodiimide (DICP; 0.93 g, 0.0073 mol) were dissolved in 20 mL of dichloromethane. The mixture was cooled in an ice-bath for five minutes. Then, a solution of N-CBZ-(D,L)-alanine (0.55 g, 0.00245 mol) in dichloromethane (10 mL) was added dropwise with stirring over a 30 minute period. The resulting mixture was allowed to stir at room temperature for an additional four hours. Next, the solid was removed by filtration and 200 mL of dichloromethane was added to the filtrate. The resulting solution was washed with water (200 mL×3) and the organic phase was dried over Na$_2$SO$_4$ and concentrated to dryness under reduced pressure. The crude product was purified by silica gel chromatography to give 1.14 g of d$_9$-docetaxel-2'-ester of N-CBZ-(D,L)-alanine as a white solid.

$^1$H NMR (CDCl$_3$): δ 8.15 (d, 2H), 7.62 (m, 1H), 7.51 (m, 2H), 7.35 (m, 10H), 6.24 (t, 1H), 5.71 (d., 1H), 5.50 (m., 2H), 5.40 (s, 1H), 5.35 (br., 1H), 5.22 (s, 1H), 5.12 (m, 2H), 4.98 (d, 1H), 4.50 (m, 1H), 4.35 (d, 1H), 4.25 (m, 1H), 4.20 (m, 2H), 3.95 (d, 1H), 2.60 (m, 1H), 2.45 (s, 3H), 2.32 (m, 1H), 2.22 (m, 1H), 1.95 (s, 3H), 1.85 (t, 1H), 1.75 (s, 3H), 1.65 (d. 1H), 1.24 (m, 6H), 1.16 (s, 3H). LC-MS (m/z): Calculated: 1021.5. found 1022.5 [M+H]$^+$.

Removal of the CBZ protective group was achieved by hydrogenation (hydrogen pressure 30 psi, 3 hour) performed in tetrahydrofuran (THF; 50 ml), in the presence of hydrogenation catalyst (10% of palladium on the active carbon; 0.50 g). Next, the mixture was filtered through a layer of Celite and the solvent was distilled off to dryness under reduced pressure. The crude product was dissolved in dichloromethane (150 mL) and the solution was washed with saturated sodium chloride (100 mL×2). Next, the solvent was distilled off to dryness under reduced pressure giving the desired d$_9$-docetaxel-2'-O-alaninate (0.85 g).

$^1$H NMR (CDCl$_3$): δ 8.14 (d, 2H), 7.63 (m, 1H), 7.51 (m, 2H), 7.40 (m, 2H), 7.30 (m, 3H), 6.27 (t, 1H), 5.52 (br., 1H), 5.45 (m, 2H), 5.00 (d, 1H), 4.85 (s, 1H), 4.32 (d, 1H), 4.20 (d, 1H), 3.90 (m, 1H), 3.85 (m, 1H), 3.65 (m, 1H), 2.46 (s, 3H), 2.32 (m, 1H), 2.22 (m, 1H), 2.00 (s, 3H), 1.80 (t, 1H), 1.72 (s, 3H), 1.22 (d, 6H), 1.15 (d, 3H). LC-MS (m/z): Calculated: 887.4. found 888.5 [M+14]$^+$.

Use of this amine in the conjugation step (e.g., Example 15) should proceed without a significant storage period. If storage over an extended period of time is anticipated, the free amine (d$_9$-docetaxel-2'-O-alaninate) may be converted into a stable salt by treatment with an equivalent amount of an appropriate acid, e.g., trifluoroacetic acid) in dichloromethane followed by solvent evaporation to dryness.

Example 14

Synthesis of $d_9$-Docetaxel-2'-O-Glycinate

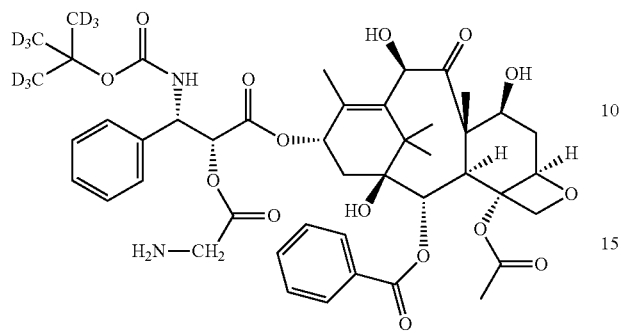

The procedure of Example 6 was repeated using instead of N-CBZ-(D,L)-alanine the same molar amount of N-CBZ-(D,L)-glycine.

The obtained $d_9$-Docetaxel-2'-O-glycinate (0.81 g) was analyzed by NMR and LC-MS: $^1$H NMR (CDCl$_3$): δ 8.14 (d, 2H), 7.62 (m, 1H), 7.51 (m, 2H), 7.42 (m, 2H), 7.32 (m, 3H), 6.25 (t, 1H), 5.70 (br., 1H), 5.52 (s, 1H), 5.45 (m, 1H), 5.25 (d, 1H), 5.00 (m, 1H), 4.30 (m, 3H), 3.95 (m, 1H), 3.70 (m, 1H), 3.60 (d, 1H), 3.50 (d, 1H), 2.60 (m, 1H), 2.40 (m, 5H), 2.00 (s, 3H), 1.80 (m, 1H), 1.75 (s, 3H), 1.25 (s, 3H), 1.15 (s, 3H). LC-MS (m/z): Calculated: 873.4. found 874.5 [M+H]$^+$.

Example 15

Synthesis of 4-ARM-PEG$_{20K}$-Alaninate-Linked $d_9$-Docetaxel Conjugate ("4-ARM-PEG$_{20K}$-CM-ALA-$d_9$-DOC")

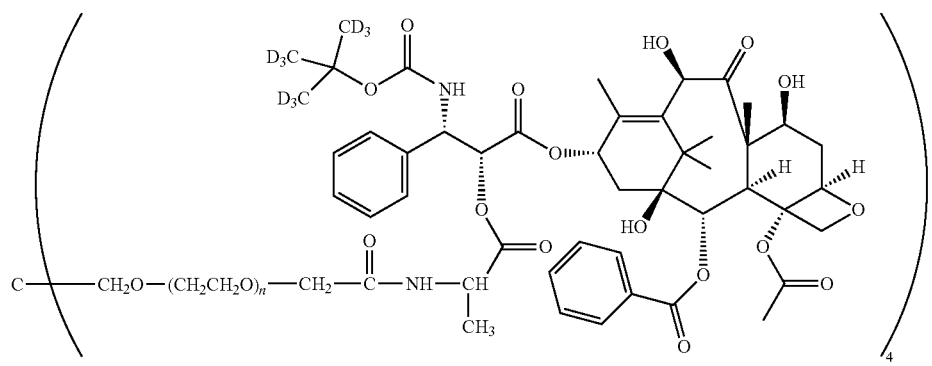

4-ARM-PEG$_{20K}$-acetic acid, N-hydroxysuccinimide ester (5.00 g, 0.00100 equivalents; Example 3) was added slowly to the solution of $d_9$-docetaxel-2'-O-alaninate (1.07 g, 0.00120 moles) in dichloromethane (50 ml). The solution was stirred at room temperature for three days. The reaction mixture was concentrated by distilling off about ⅔ of dichloromethane under reduced pressure and the product was precipitated with isopropyl alcohol/ethyl ether mixture (1:1, 250 mL). Next, the product was reprecipitated using the same mixture of solvents giving after drying 4.1 g of a white solid. NMR analysis of the product in CDCl$_3$ as a solvent showed that to each molecule of 4ARM-PEG$_{20K}$-alaninate (4-ARM-PEG$_{20K}$-CM-ALA) was connected ~4 molecules of $d_9$-docetaxel.

$^1$H NMR (CDCl$_3$): δ 8.13 (d, 8H), 7.60 (m, 4H), 7.50 (m, 8H), 7.40 (m, 8H), 7.30 (m, 8H), 6.25 (m, 4H), 5.65 (m, 4H), 5.50 (br., 4H), 5.38 (s, 4H), 5.00 (d, 4H), 4.30 (d, 4H), 4.15 (d, 4H), 3.95 (d, 4H), 3.80-3.46 (m, 2463H), 2.60 (m, 4H), 2.42 (s, 12H), 2.32 (m, 4H), 2.22 (m, 4H), 2.00 (s, 12H), 1.80 (t, 4H), 1.70 (s, 12H), 1.65 (m, 8H), 1.23 (s, 12H) 1.14 (s, 12H).

Example 16

Synthesis of 4-ARM-PEG$_{20K}$-Glycinate-Linked d9-Docetaxel Conjugate ("4-ARM-PEG$_{20K}$-GLY-d$_9$-DOC")

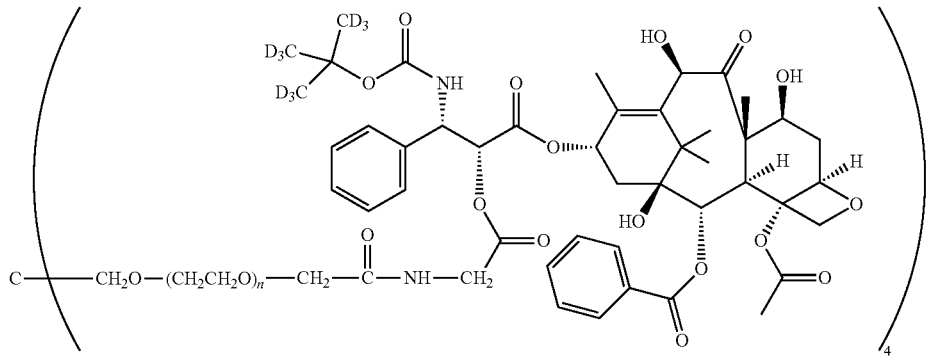

The procedure of Example 15 was repeated using instead of d$_9$-docetaxel-2'-O-alaninate, the same molar amount of d$_9$-docetaxel-2'-O-glycinate. NMR analysis of the obtained product showed that to each molecule of 4ARM-PEG$_{20K}$-glycinate (4-ARM-PEG$_{20K}$-CM-GLY) was connected ~4 molecules of d$_9$-docetaxel.

$^1$H NMR (500 MHz, CDCl$_3$): δ 8.12 (d, 8H), 7.70 (br., 4H), 7.60 (m, 4H), 7.50 (m, 8H), 7.40 (m, 8H), 7.30 (m, 8H), 6.25 (t, 4H), 5.74 (br., 8H), 5.50 (br., 4H), 5.38 (s, 4H), 5.24 (s, 4H), 5.00 (d, 4H), 4.30 (d, 4H), 4.22 (d, 4H), 4.15 (m, 8H), 4.00 (d, 4H), 3.90 (m, 4H), 3.85-3.50 (m, 2025H), 2.60 (m, 4H), 2.40 (s, 12H), 2.32 (m, 4H), 2.22 (m, 4H), 2.00 (s, 12H), 1.85 (m, 8H), 1.75 (s, 12H), 1.25 (s, 12H), 1.15 (s, 12H).

Example 17

Synthesis of 4-ARM-PEG$_{20K}$-Butanoate-Linked d$_9$-Docetaxel Conjugate ("4-ARM-PEG$_{20K}$-BA-d$_9$-DOC")

To a solution of 4-ARM-PEG$_{20K}$-butanoic acid (6.0 g, 0.00120 equivalents, Example 1), d$_9$-docetaxel (1.08 g, 0.00132 moles), and p-toluenosulfonic acid 4-dimethylaminopyridine salt (0.372 g, 0.00120 moles) in 60 ml of anhydrous dichloromethane was added N,N'-diisopropylcarbodiimide (0.454 g, 0.00360 mole) and the mixture was stirred overnight at room temperature under an nitrogen atmosphere. The reaction mixture was concentrated by distilling off about ⅔ of dichloromethane under reduced pressure and the product was precipitated with isopropyl alcohol/ethyl ether mixture (1:1, 400 mL). Next, the product was reprecipitated using the same mixture of solvents giving after drying 5.5 g of a white solid. NMR analysis of the product in CDCl$_3$ as a solvent showed that to each molecule of 4-ARM-PEG$_{20K}$-butanoic acid (4-ARM-PEG$_{20K}$-BA) was connected ~4 molecules of d$_9$-docetaxel.

$^1$H NMR (CDCl$_3$): δ 8.12 (d, 8H), 7.58 (m, 4H), 7.44 (m, 8H), 7.30 (m, 8H), 7.24 (m, 8H), 6.25 (m, 4H), 5.66 (d, 4H), 5.50 (m, 8H), 5.35 (s, 4H), 5.20 (s, 4H), 5.00 (d, 4H), 4.30 (d, 4H), 4.25 (d, 4H), 4.20 (m, 4H), 3.90 (d, 4H), 3.80-3.40

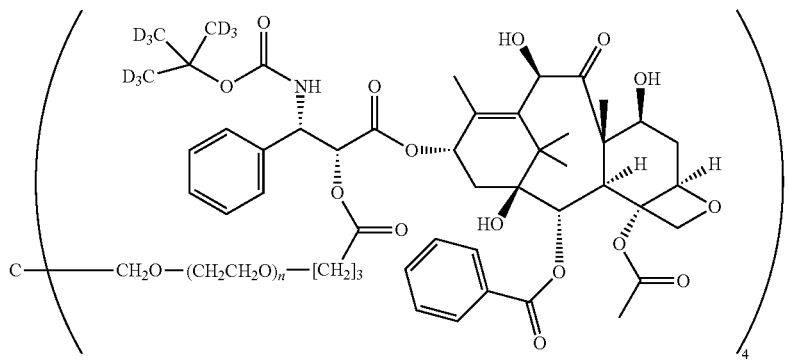

(m, 2017H), 2.60 (m, 8H), 2.45 (m, 14H), 2.30 (m, 4H), 2.15 (m, 4H), 2.00 (s, 12H), 1.85 (m, 12H), 1.75 (s, 12H), 1.20 (s, 12H), 1.12 (s, 12H).

Example 18

Maximum Tolerated Doses (MTD) of Conjugates of $d_9$-Docetaxel in Athymic Mice

MTD for 4-arm-PEG20K-CM-glycine-$d_9$-docetaxel and 4-arm-PEG20K-BA-$d_9$-docetaxel were determined in female athymic nu/nu mice using standard methods. Briefly, 8-12 week old mice were administered test compounds or $d_9$-docetaxel intravenously (iv) as shown in Table 1. For all test compounds, the dose refers to the $d_9$-docetaxel content. $d_9$-Docetaxel solutions were prepared in D5W containing 7.5% Tween 80:7.5% ethanol. PEG-$d_9$-docetaxel conjugates were prepared in D5W. The administration volume for all test articles was 10 mL/kg. Mice were observed daily for clinical signs and body weights were recorded on days 1-5 and then biweekly until the end of study. Any individual animal with a single observation of greater than 30% body weight loss or three consecutive measurements of greater than 25% body weight loss was euthanized. For any group with two measurements of mean body weight loss of greater than 20%, dosing was stopped and recovery was allowed. Within a group with greater than 20% mean weight loss, individual animals greater than 30% body weight loss were euthanized. Compound dosing was terminated for any group in which mean weight loss exceeded 20% or >10% of animals died. Moribund animals were euthanized and all animals were euthanized at end of study.

TABLE 1

Maximum Tolerated Dose (MTD) Study Treatment Plan

| Treatment Group | N | Test article | Dose, mg/kg | Route | Schedule |
|---|---|---|---|---|---|
| 1 | 5 | Docetaxel-$d_9$ | 25 | iv | qwk x 3 |
| 2 | 5 | 4-ARM-PEG$_{20K}$-CM-GLY-$d_9$-DOC | 7.5 | iv | qwk x 3 |
| 3 | 5 | 4-ARM-PEG$_{20K}$-CM-GLY-$d_9$-DOC | 15 | iv | qwk x 3 |
| 4 | 5 | 4-ARM-PEG$_{20K}$-CM-GLY-$d_9$-DOC | 30 | iv | qwk x 3 |
| 5 | 5 | 4-ARM-PEG$_{20K}$-BA-$d_9$-DOC | 7.5 | iv | qwk x 3 |
| 6 | 5 | 4-ARM-PEG$_{20K}$-BA-$d_9$-DOC | 15 | iv | qwk x 3 |
| 7 | 5 | 4-ARM-PEG$_{20K}$-BA-$d_9$-DOC | 30 | iv | qwk x 3 |

Study results are summarized in Table 2 and in FIG. 1. Body weight loss >15% of initial body weight is typically the maximum desired for tumor xenograft experiments. Weight loss for $D_9$-docetaxel treated animals was consistent with that observed in a previous MTD study. Based upon the current study data, it is estimated that the MTD are 20 mg/kg for both 4-ARM-PEG$_{20K}$-butanoate-linked $d_9$-docetaxel and 4-ARM-PEG$_{20K}$-CM-glycinate-linked-$d_9$-docetaxel in athymic nu/nu mice, when the test articles are administered qwk×3, iv.

TABLE 2

Summary of Body Weight Loss Following Treatment with Various Test Articles

| Treatment Group | N | Test article | Dose, mg/kg | Body Weight Nadir (day) | Treatment-Related Deaths | Mean Day of Death |
|---|---|---|---|---|---|---|
| 1 | 5 | Docetaxel-$d_9$ | 25 | −17.7% (21) | 0 | — |
| 2 | 5 | 4ARM-PEG$_{20K}$-CM-GLY-$d_9$-DOC | 7.5 | −1.6% (2) | 0 | — |
| 3 | 5 | 4ARM-PEG$_{20K}$-CM-GLY-$d_9$-DOC | 15 | −4.2% (10) | 0 | — |
| 4 | 5 | 4ARM-PEG$_{20K}$-CM-GLY-$d_9$-DOC | 30 | −25.2% (21) | 0 | — |
| 5 | 5 | 4ARM-PEG$_{20K}$-BA-$d_9$-DOC | 7.5 | −0.6% (2) | 0 | — |
| 6 | 5 | 4ARM-PEG$_{20K}$-BA-$d_9$-DOC | 15 | — | 0 | — |
| 7 | 5 | 4ARM-PEG$_{20K}$-BA-$d_9$-DOC | 30 | −21.0% (21) | 0 | — |

The invention(s) set forth herein has been described with respect to particular exemplified embodiments. However, the foregoing description is not intended to limit the invention to the exemplified embodiments, and the skilled artisan should recognize that variations can be made within the spirit and scope of the invention as described in the foregoing specification.

What is claimed is:

1. A conjugate of formula:

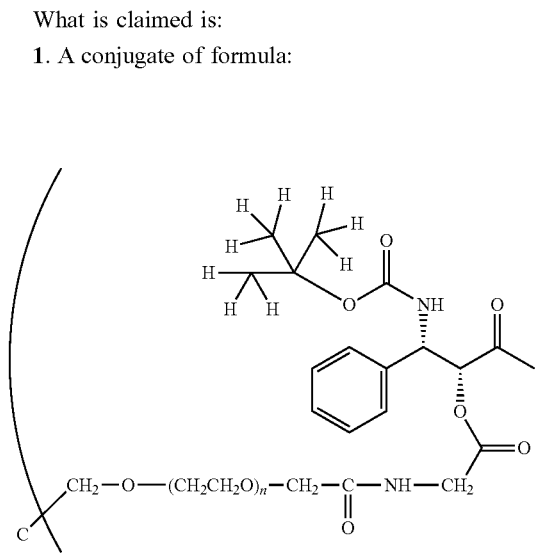

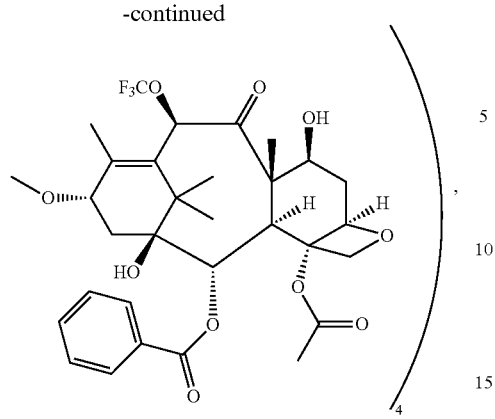
wherein n is a positive integer from 10 to about 400, or a pharmaceutically acceptable salt thereof.
2. A composition comprising a plurality of conjugates, wherein at least 80% of the conjugates in the composition have a structure encompassed by claim 1.
3. The composition of claim 2, further comprising a pharmaceutical excipient.
* * * * *